US008303617B2

(12) United States Patent
Brady et al.

(10) Patent No.: US 8,303,617 B2
(45) Date of Patent: Nov. 6, 2012

(54) EMBOLIC PROTECTION SYSTEM

(75) Inventors: Eamon Brady, Elphin (IE); Charles Taylor, Warninglid (GB); Patrick Griffin, Castlegar (IE); Brendan Casey, Barna (IE); David Vale, Clontarf (IE); Paul Gilson, Uggool Moycullen (IE); John O'Shaughnessy, Barna (IE)

(73) Assignee: Salviac Limited, Dublin (IE)

( * ) Notice: Subject to any disclaimer, the term of this patent is extended or adjusted under 35 U.S.C. 154(b) by 1367 days.

(21) Appl. No.: 10/436,328

(22) Filed: May 13, 2003

(65) Prior Publication Data

US 2003/0212431 A1 Nov. 13, 2003

Related U.S. Application Data

(60) Provisional application No. 60/379,396, filed on May 13, 2002, provisional application No. 60/412,545, filed on Sep. 23, 2002.

(51) Int. Cl.
*A61F 2/01* (2006.01)

(52) U.S. Cl. ...................................... 606/200; 623/1.11

(58) Field of Classification Search .......... 606/191–200; 623/1.11, 1.12, 1.23, 23.72
See application file for complete search history.

(56) References Cited

U.S. PATENT DOCUMENTS

| 4,545,390 | A | * | 10/1985 | Leary | 600/462 |
|---|---|---|---|---|---|
| 5,026,377 | A | * | 6/1991 | Burton et al. | 606/108 |
| 5,453,090 | A | * | 9/1995 | Martinez et al. | 606/108 |
| 5,755,777 | A | * | 5/1998 | Chuter | 623/1.11 |
| 5,827,321 | A | | 10/1998 | Roubin et al. | |
| 5,827,324 | A | * | 10/1998 | Cassell et al. | 606/200 |
| 5,910,154 | A | * | 6/1999 | Tsugita et al. | 606/200 |
| 5,941,896 | A | * | 8/1999 | Kerr | 606/200 |
| 6,336,934 | B1 | * | 1/2002 | Gilson et al. | 606/200 |
| 6,361,546 | B1 | | 3/2002 | Khosravi | |
| 6,371,971 | B1 | * | 4/2002 | Tsugita et al. | 606/200 |
| 6,375,670 | B1 | * | 4/2002 | Greenhalgh | 606/200 |
| 6,383,206 | B1 | * | 5/2002 | Gillick et al. | 606/200 |
| 6,485,501 | B1 | * | 11/2002 | Green | 606/200 |
| 6,887,256 | B2 | * | 5/2005 | Gilson et al. | 606/200 |
| 6,979,343 | B2 | * | 12/2005 | Russo et al. | 606/200 |
| 2001/0044634 | A1 | | 11/2001 | Don Michael et al. | |
| 2002/0052626 | A1 | | 5/2002 | Gilson et al. | |
| 2002/0058911 | A1 | | 5/2002 | Gilson et al. | |
| 2002/0062133 | A1 | | 5/2002 | Gilson et al. | |
| 2002/0095171 | A1 | | 7/2002 | Belef | |
| 2002/0107541 | A1 | | 8/2002 | Vale et al. | |

FOREIGN PATENT DOCUMENTS

WO WO 98/47447 10/1998
WO WO 98/50103 11/1998

\* cited by examiner

*Primary Examiner* — Kathleen Sonnett
(74) *Attorney, Agent, or Firm* — Sughrue Mion, PLLC; Jonathan Feuchtwang

(57) ABSTRACT

A catheter system 1 has an internal reception space for an embolic protection filter 10 to enable the filter 10 to be transported through a vasculature 20 and a treatment means such as a stent 15 to facilitate treatment. The catheter system may be used for retrieval of a filter 10 and stenting of a lesion with a stent 15. The procedure may also involve post dilatation using an on-board balloon 16.

33 Claims, 24 Drawing Sheets

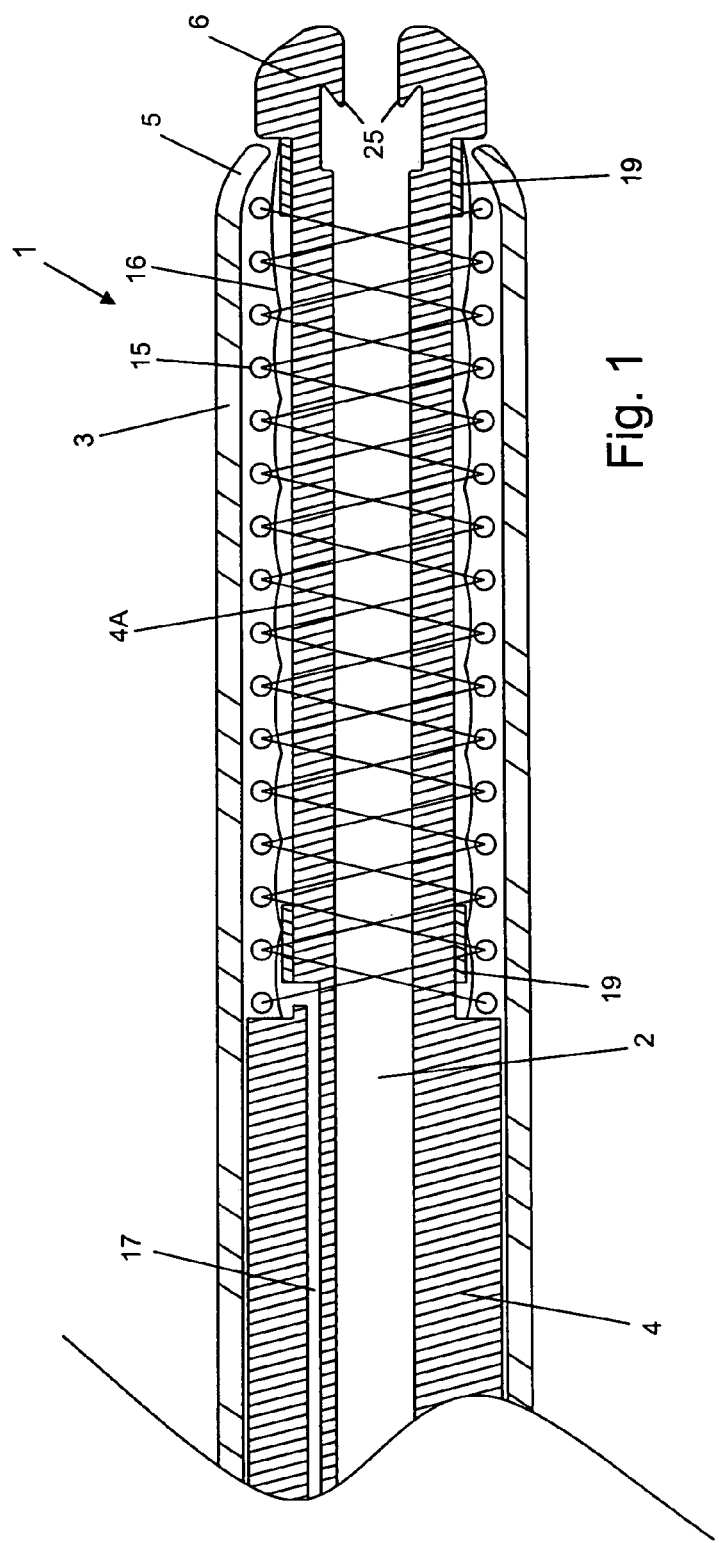

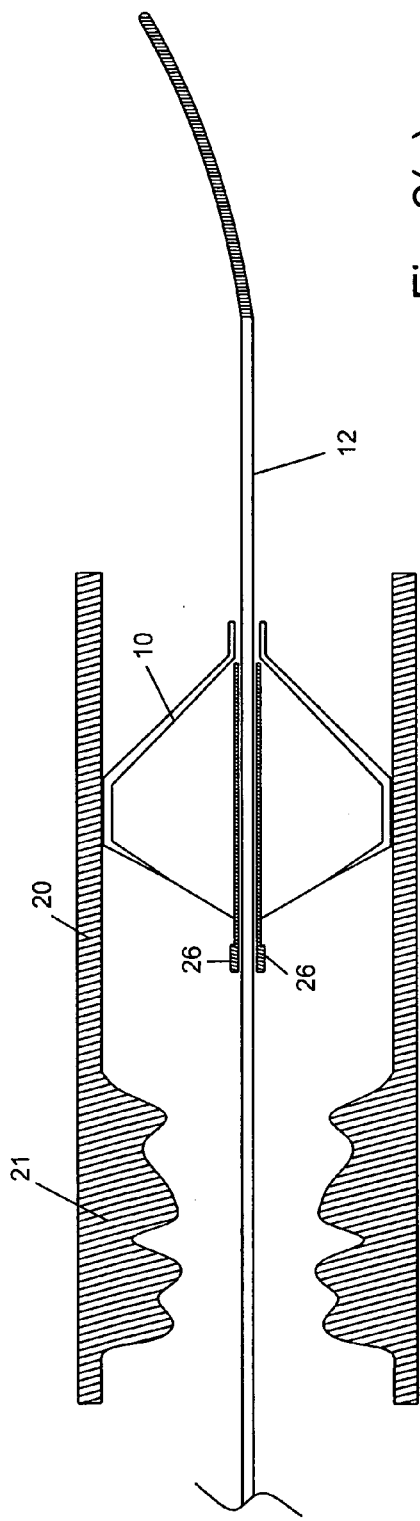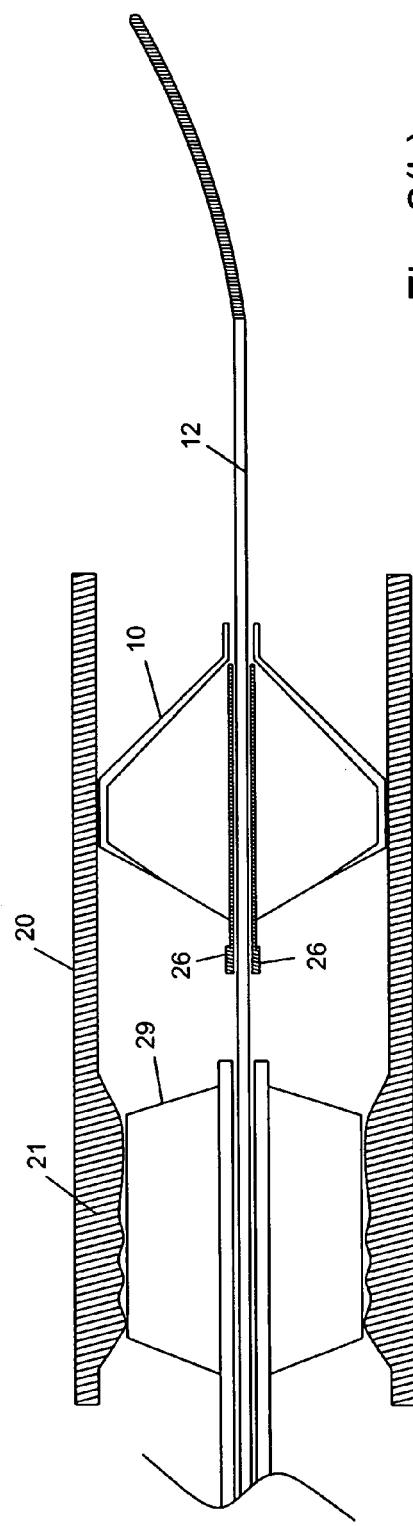

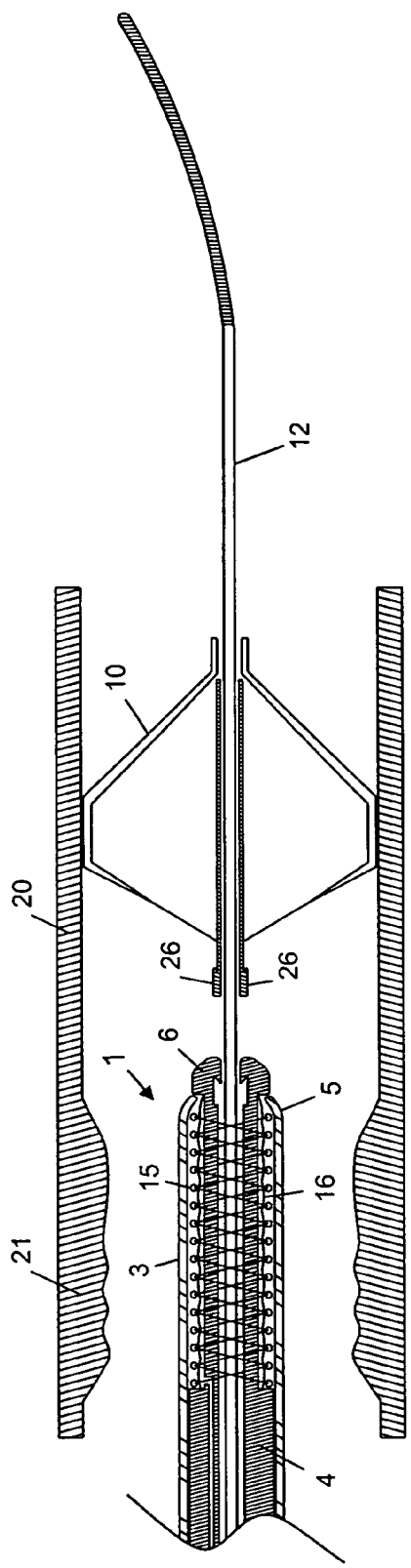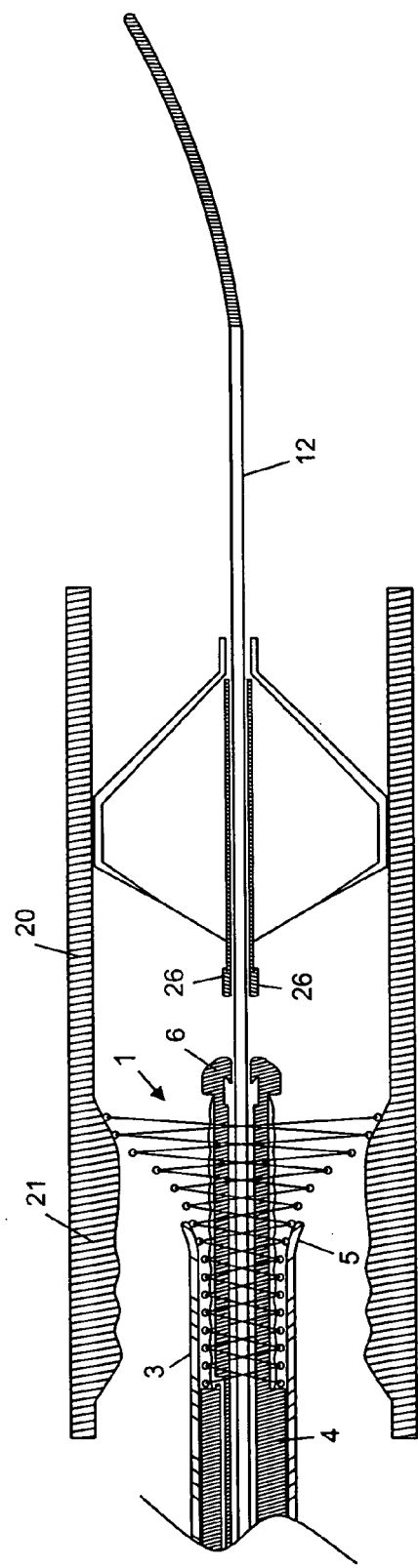

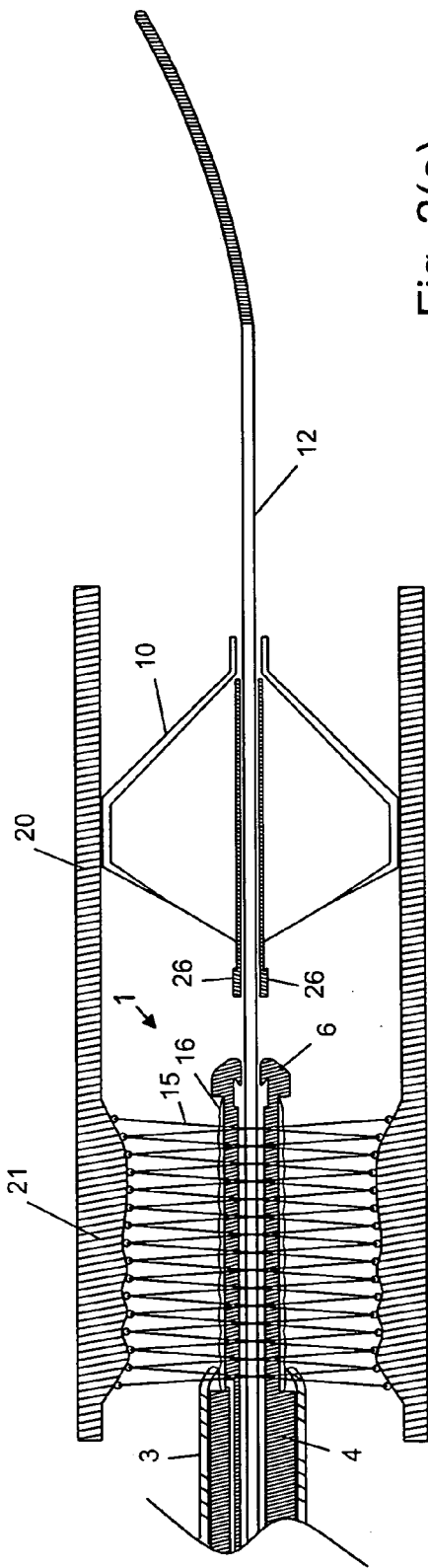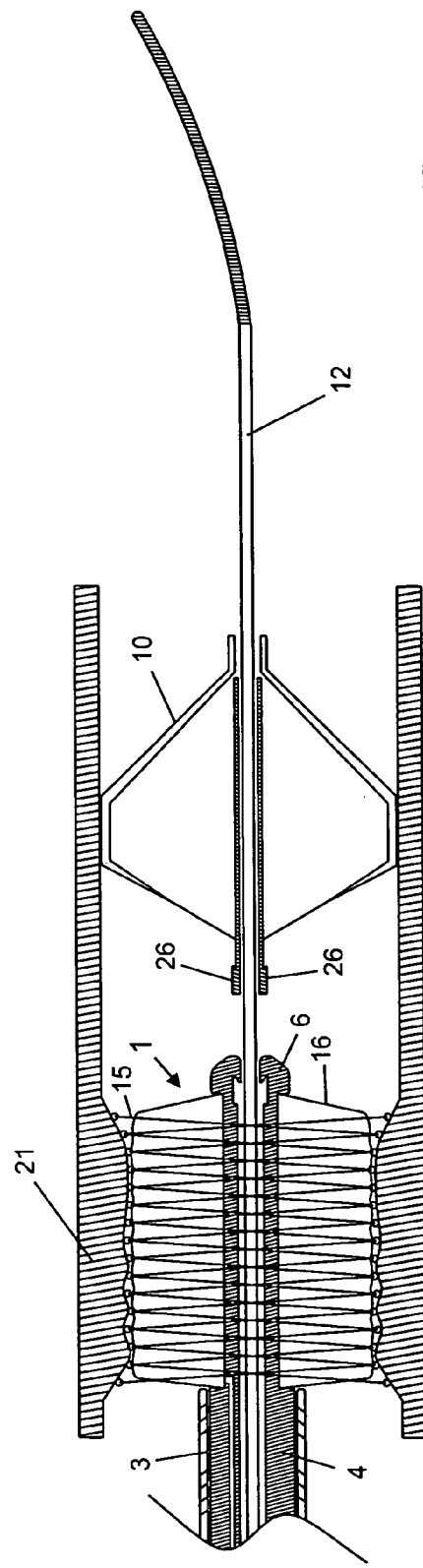

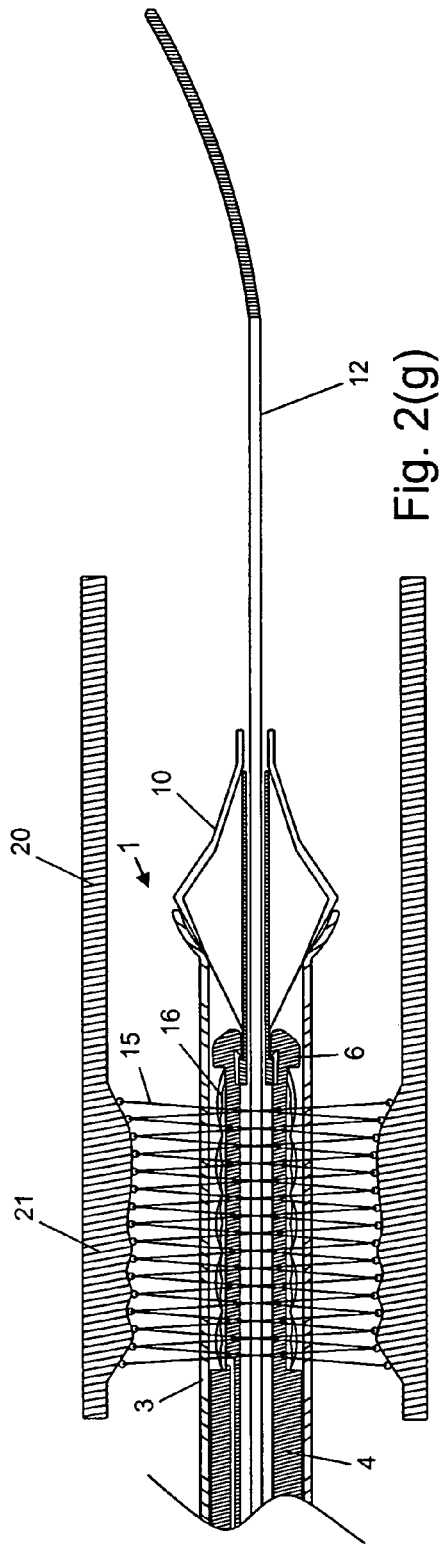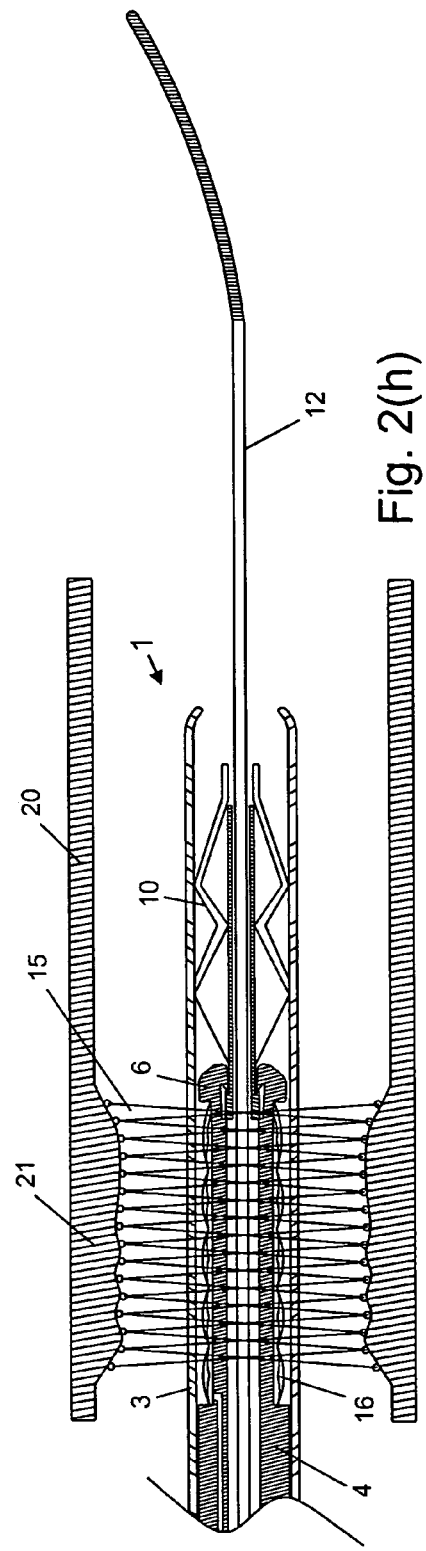

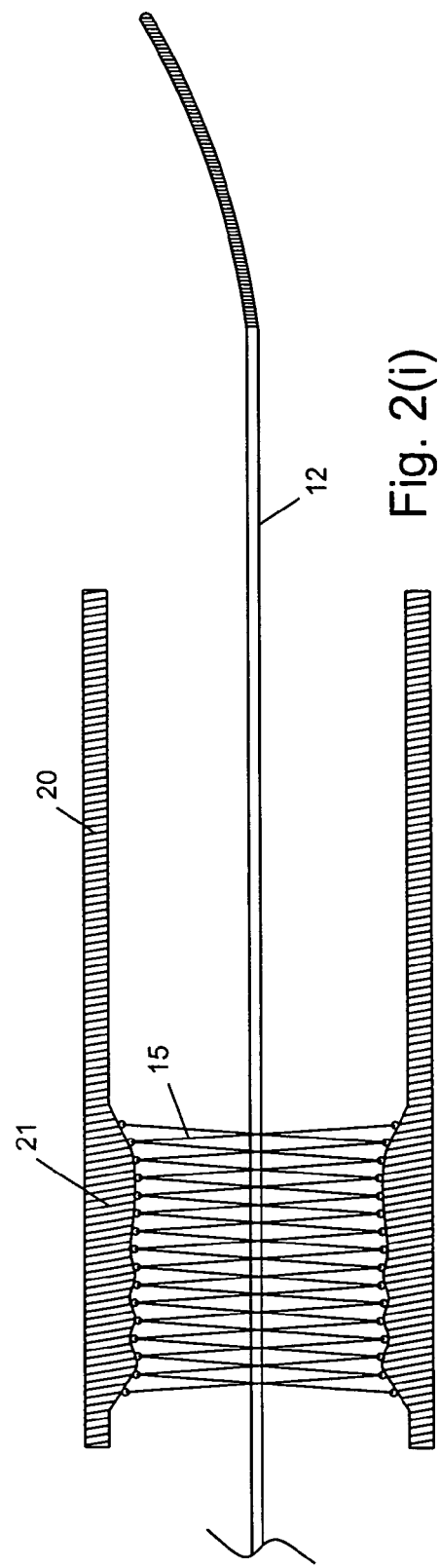

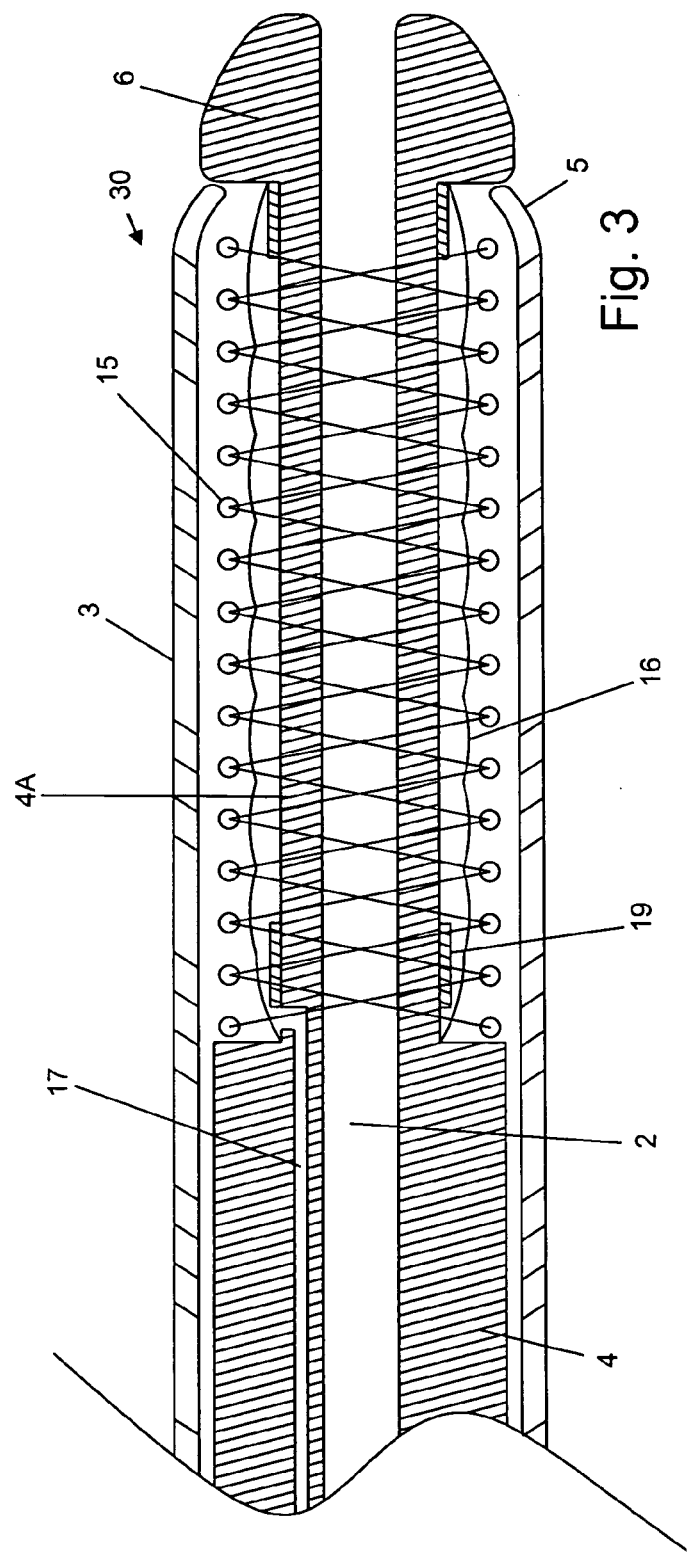

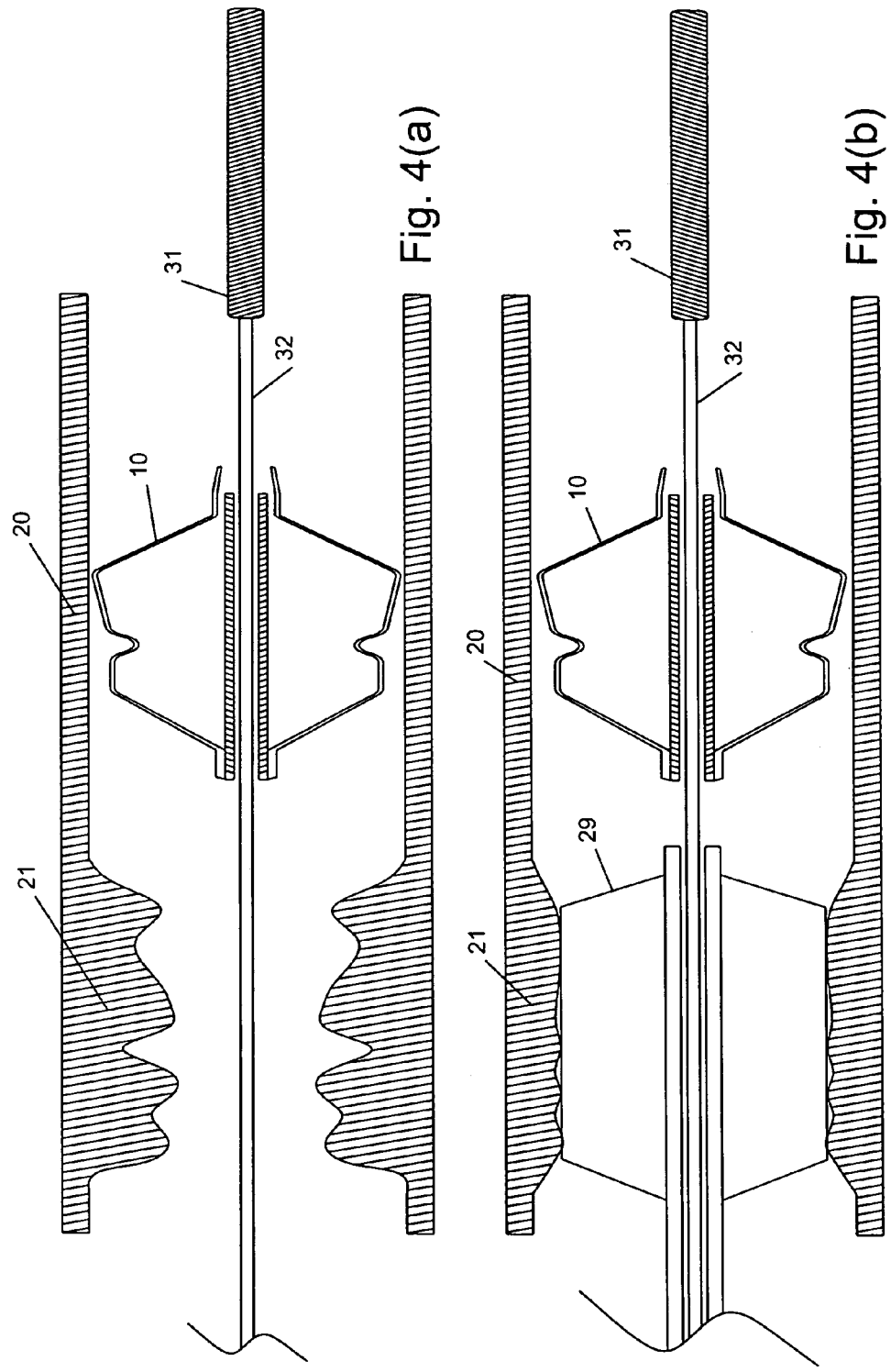

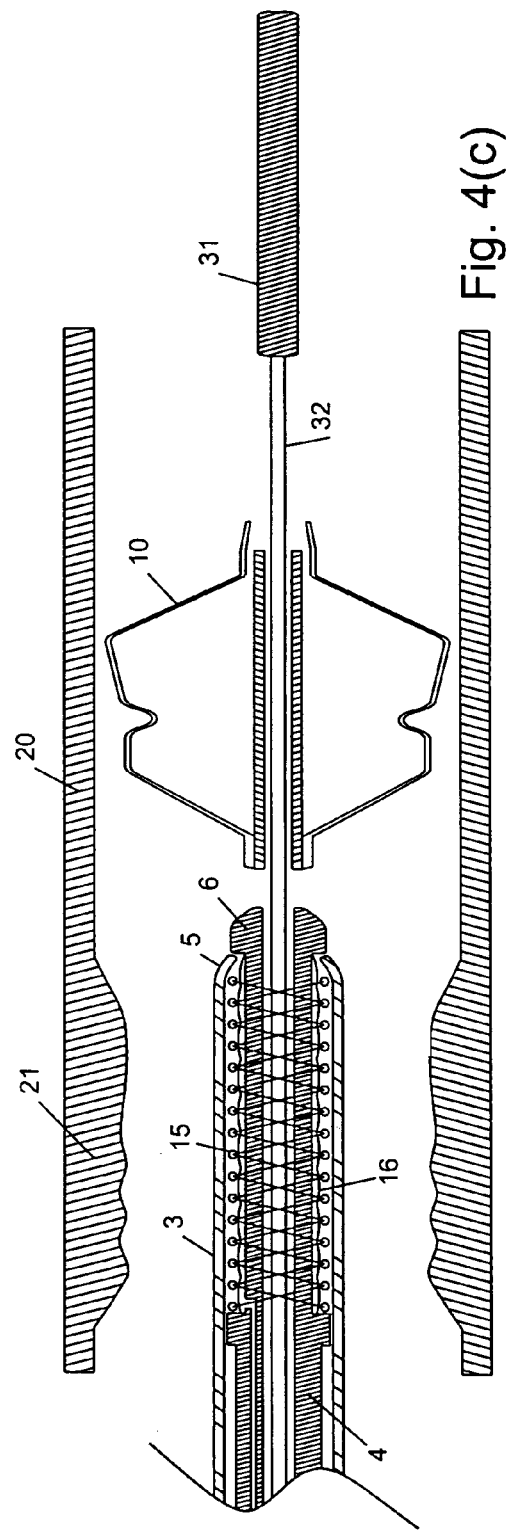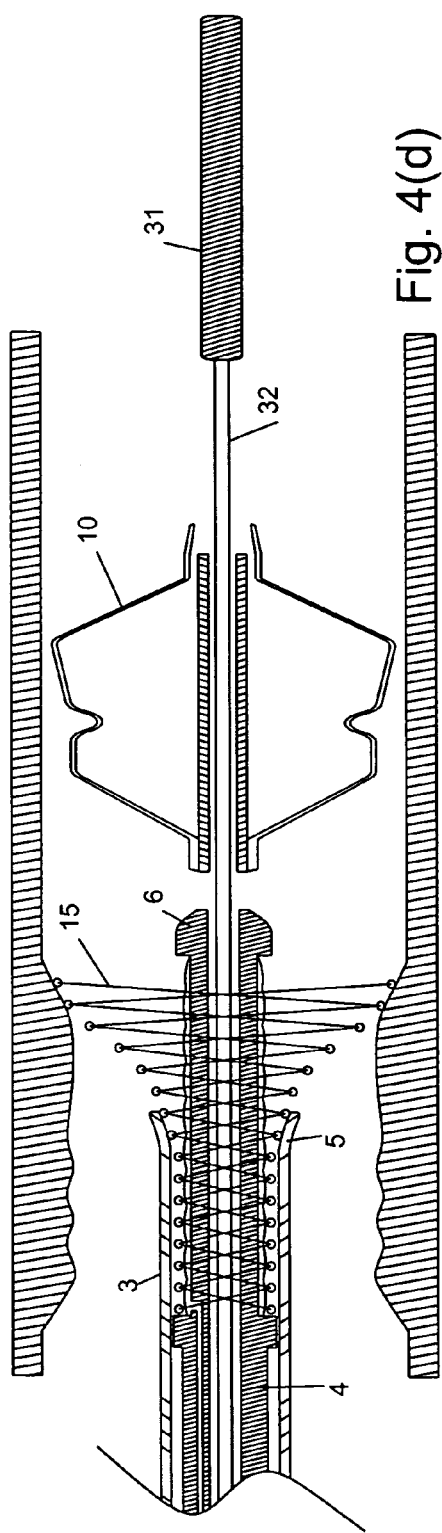

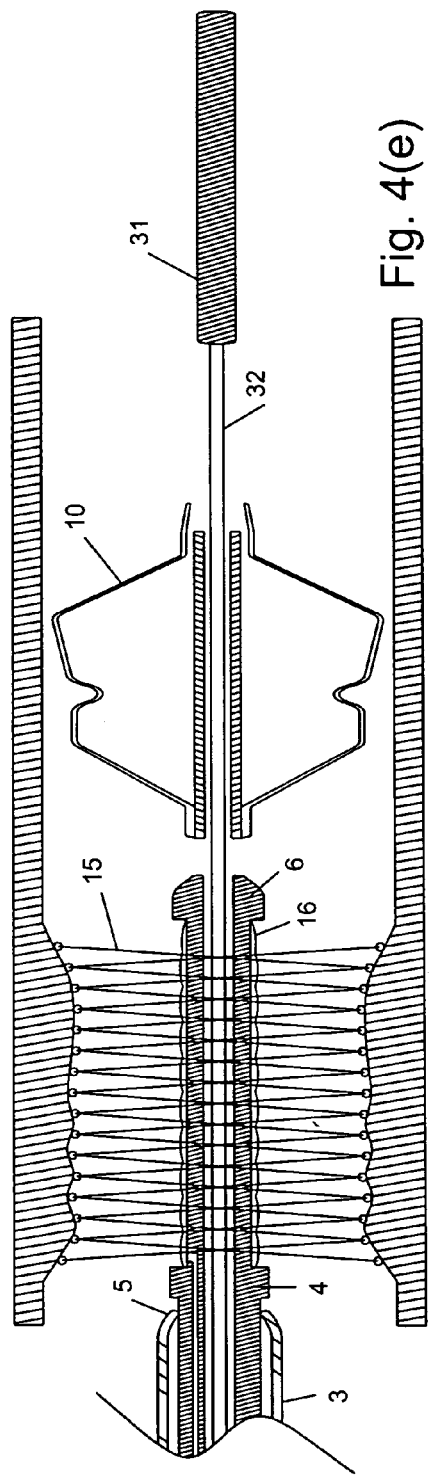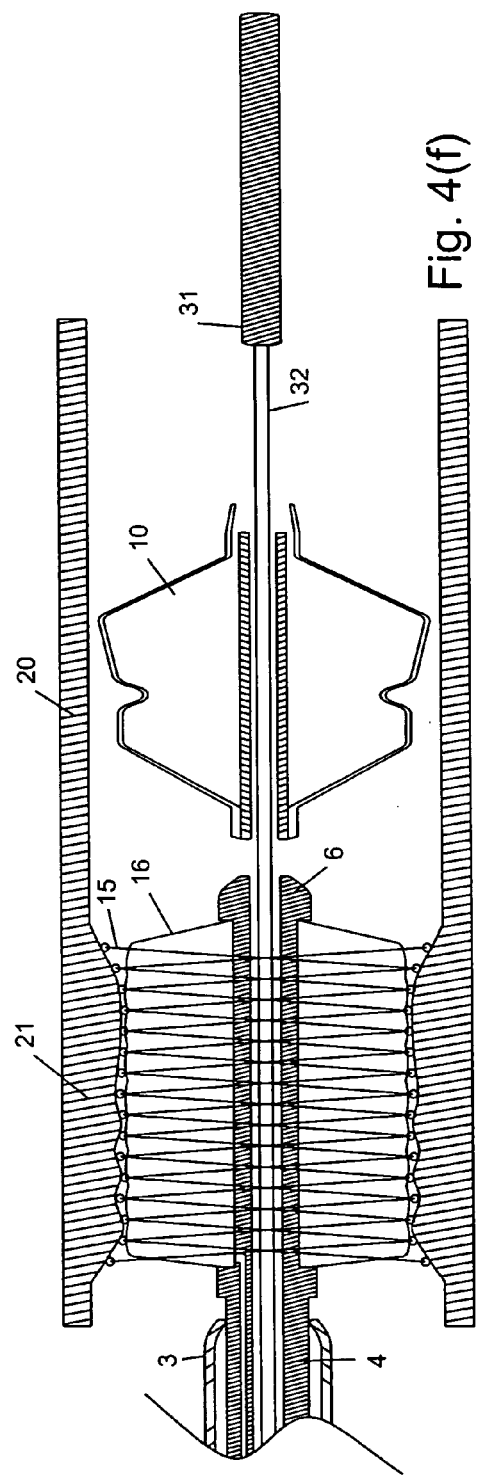

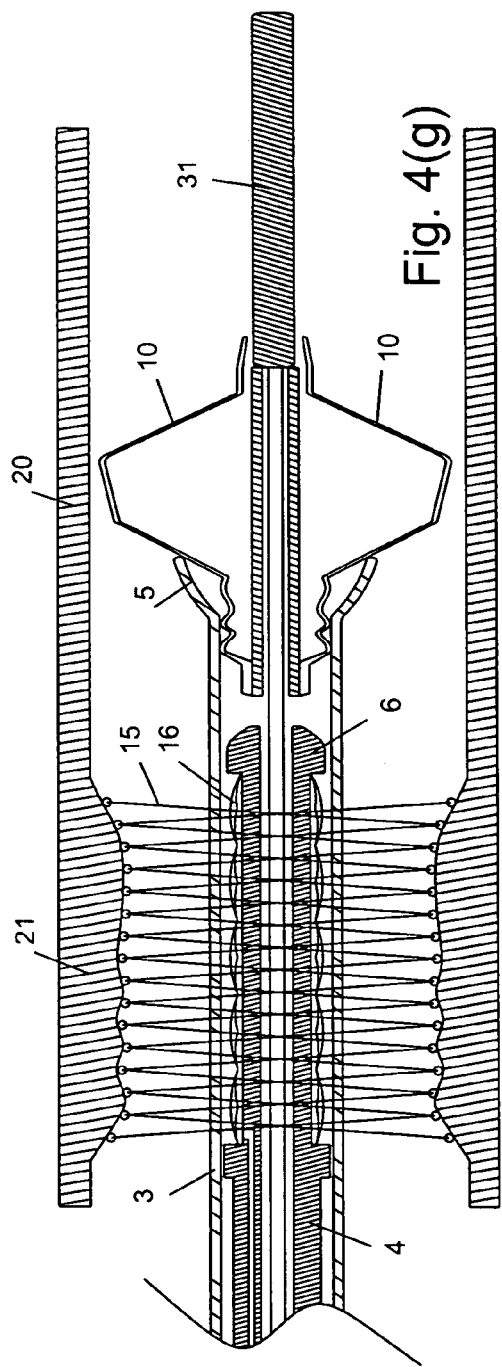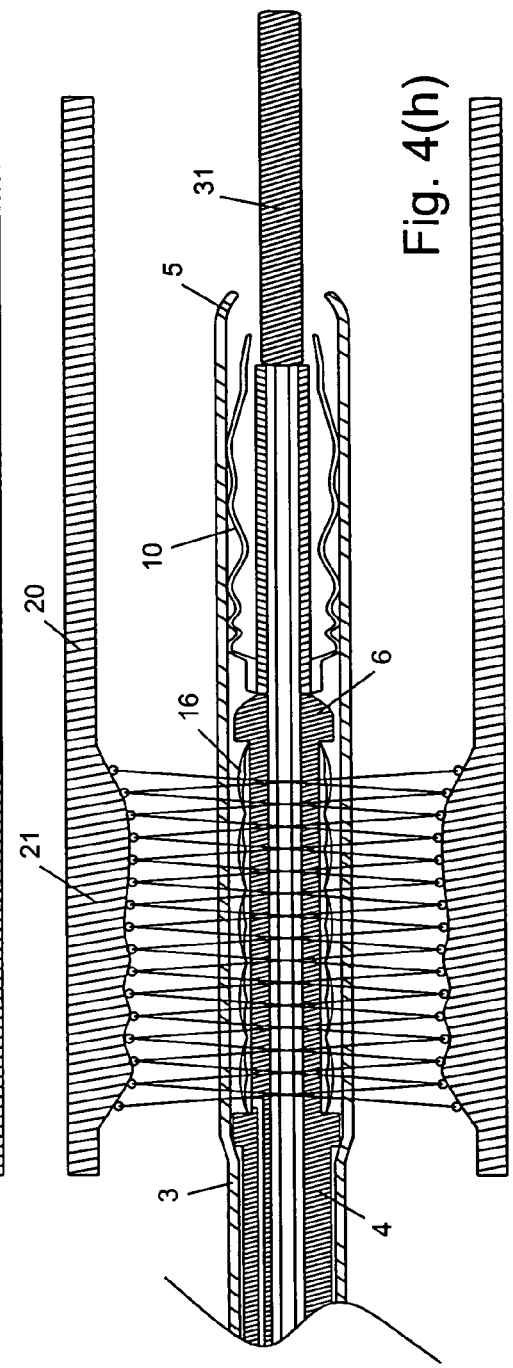

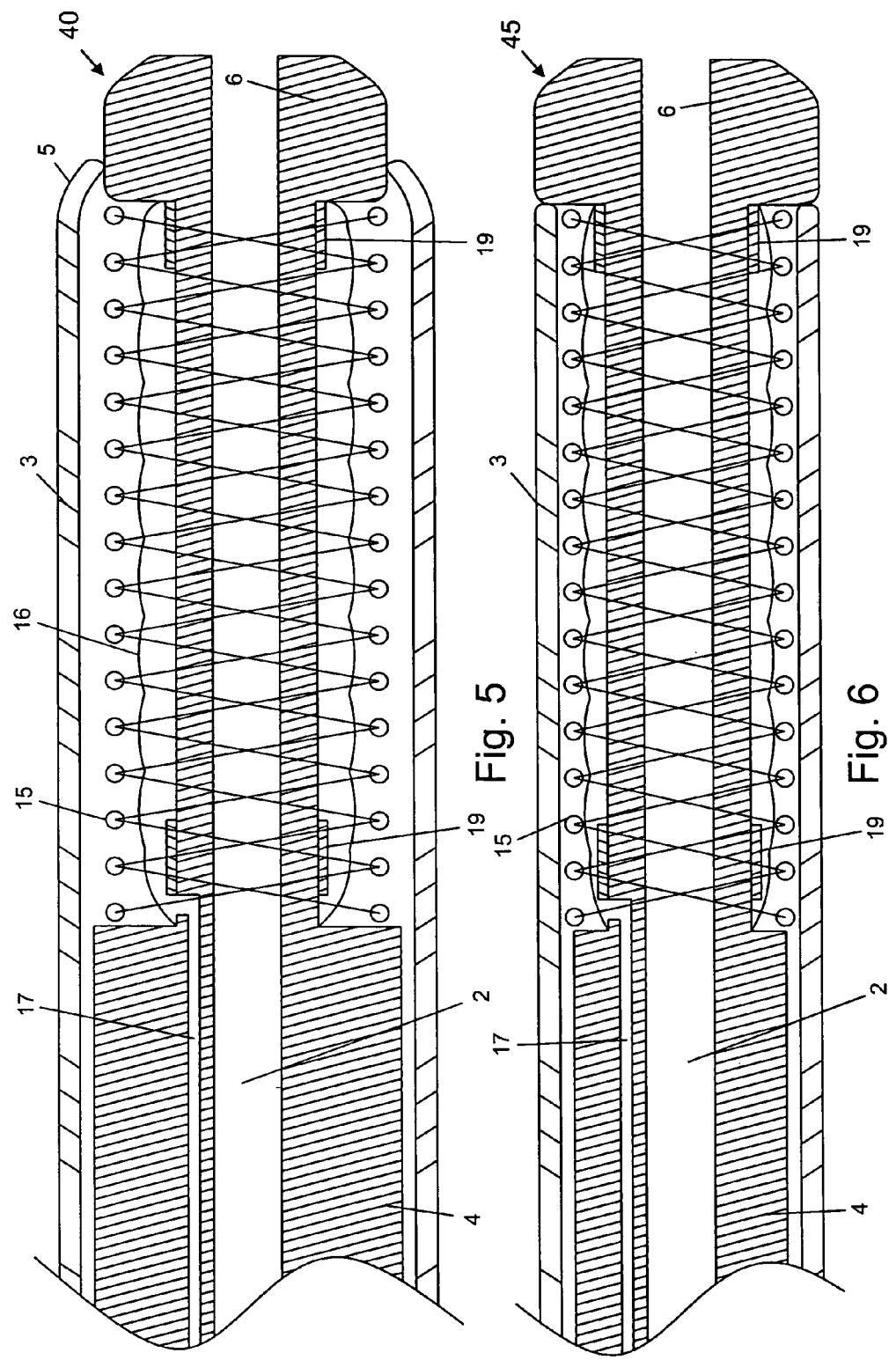

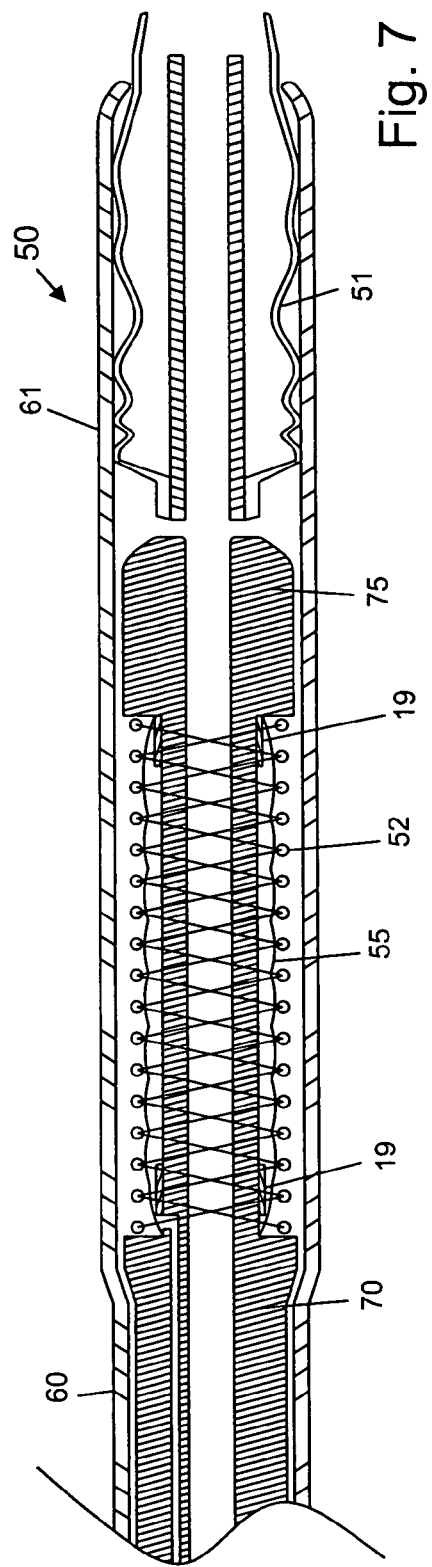

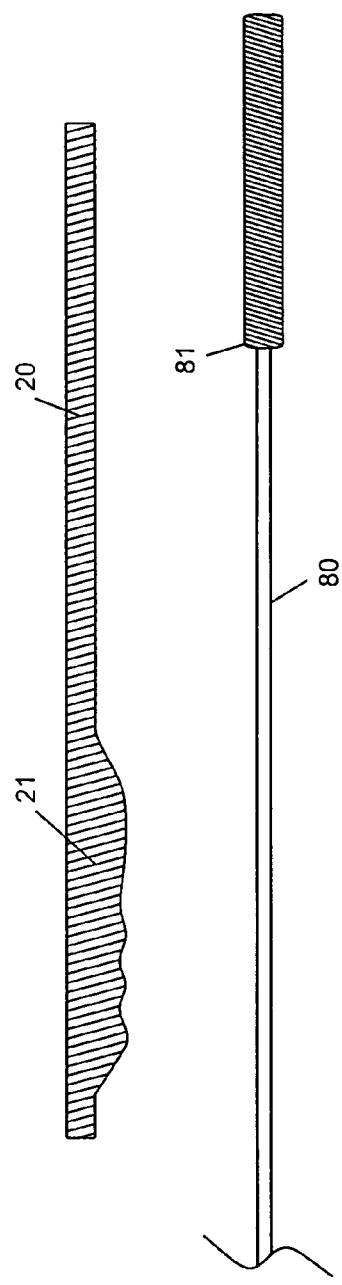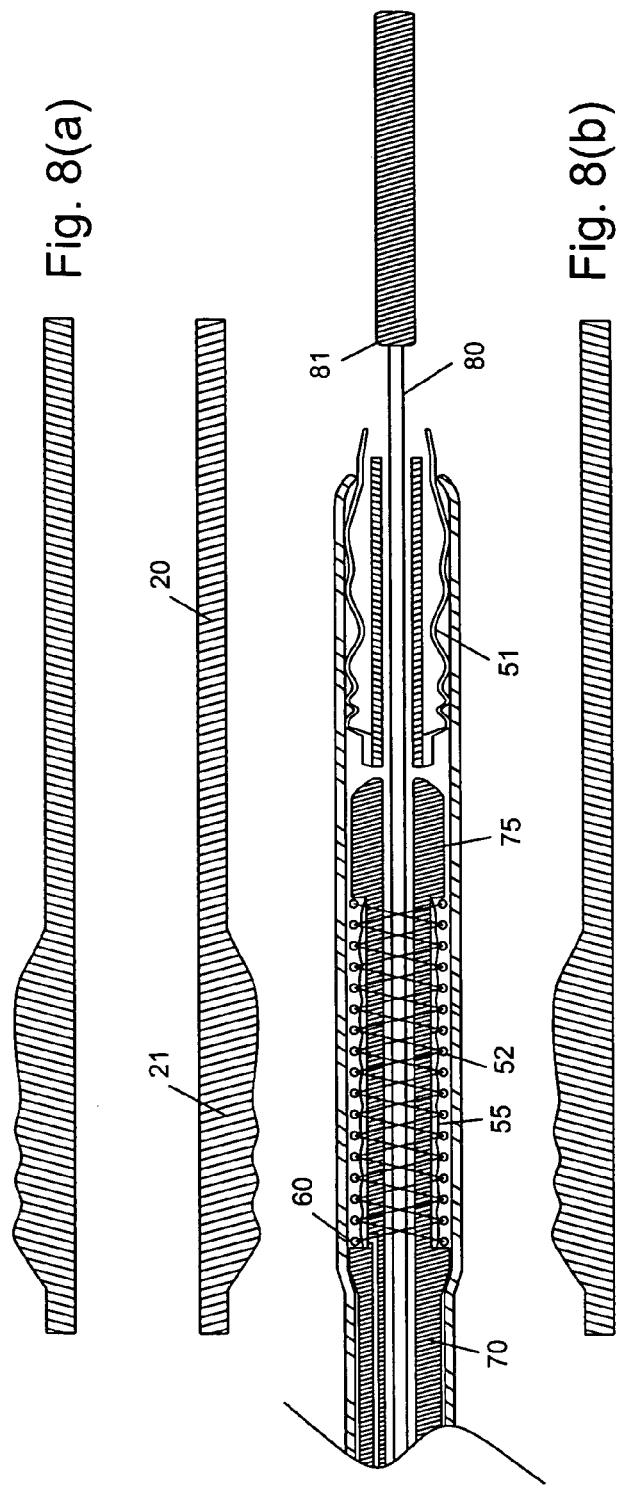

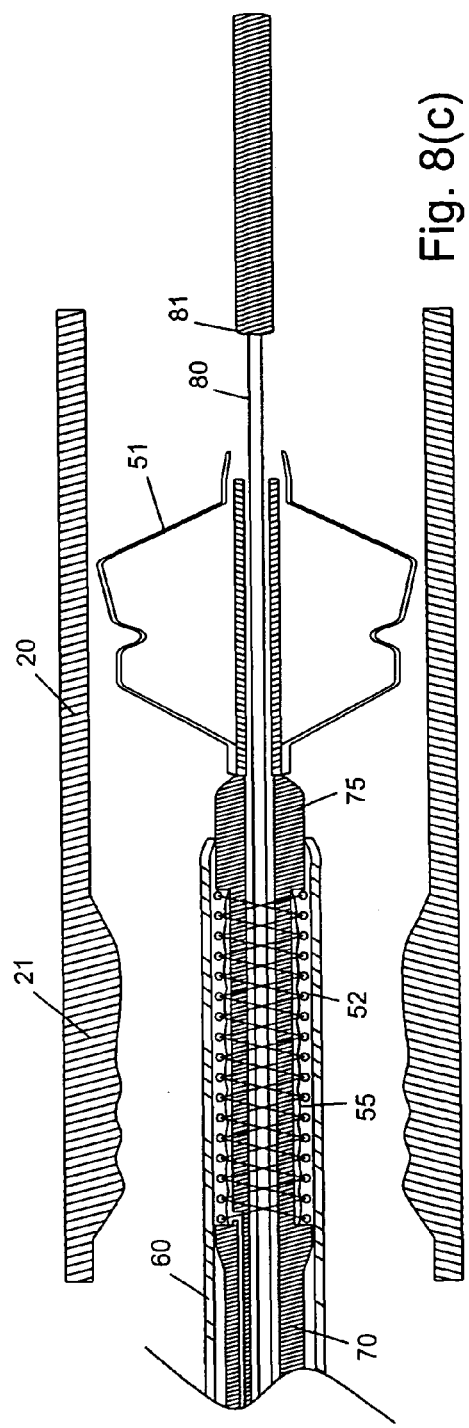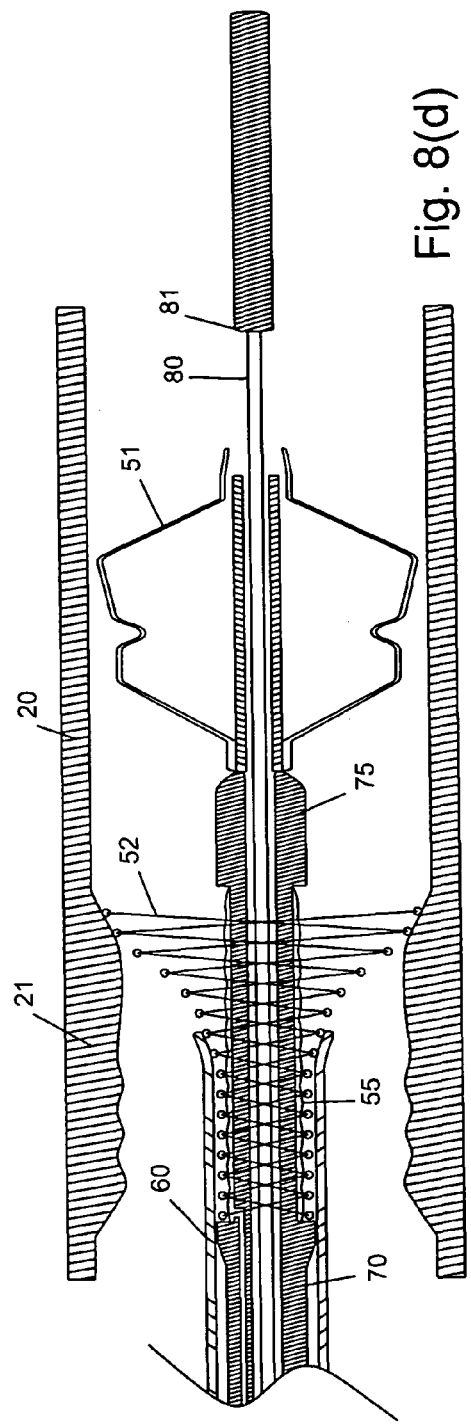

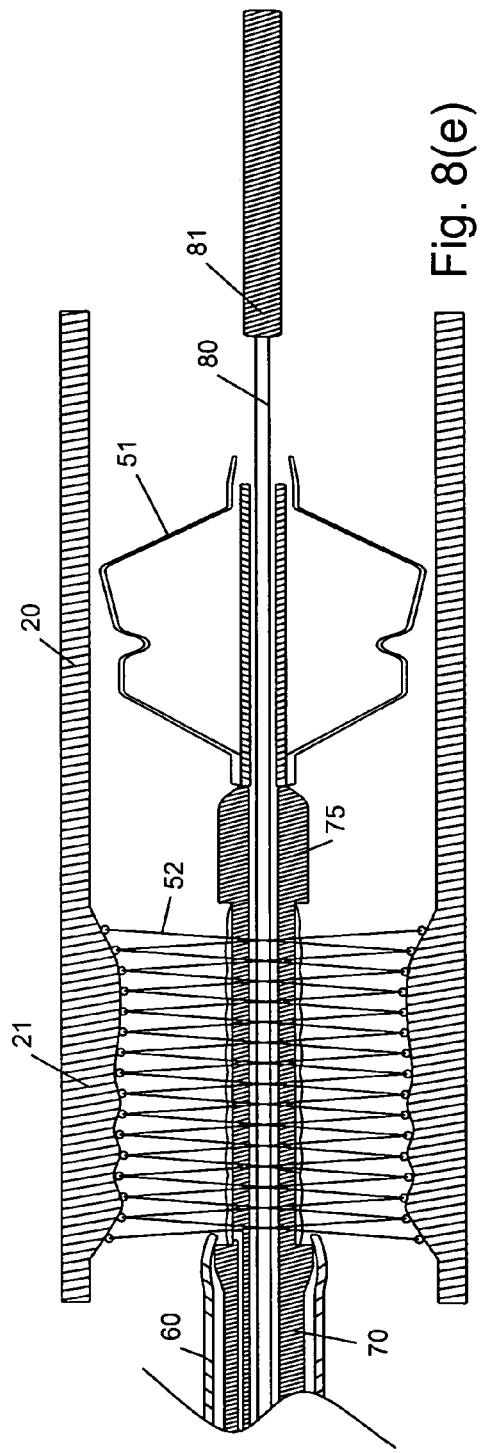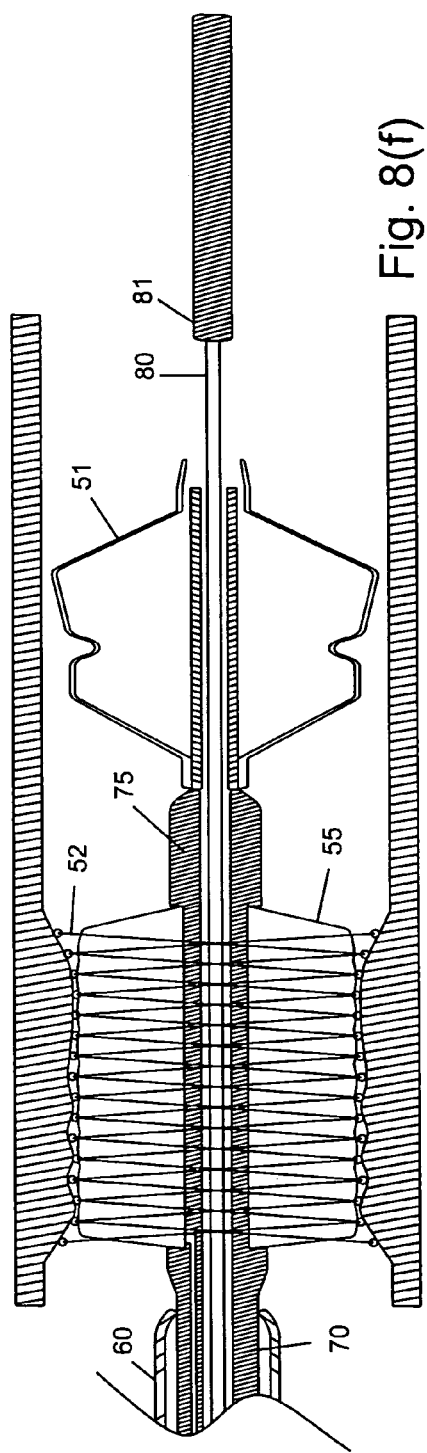

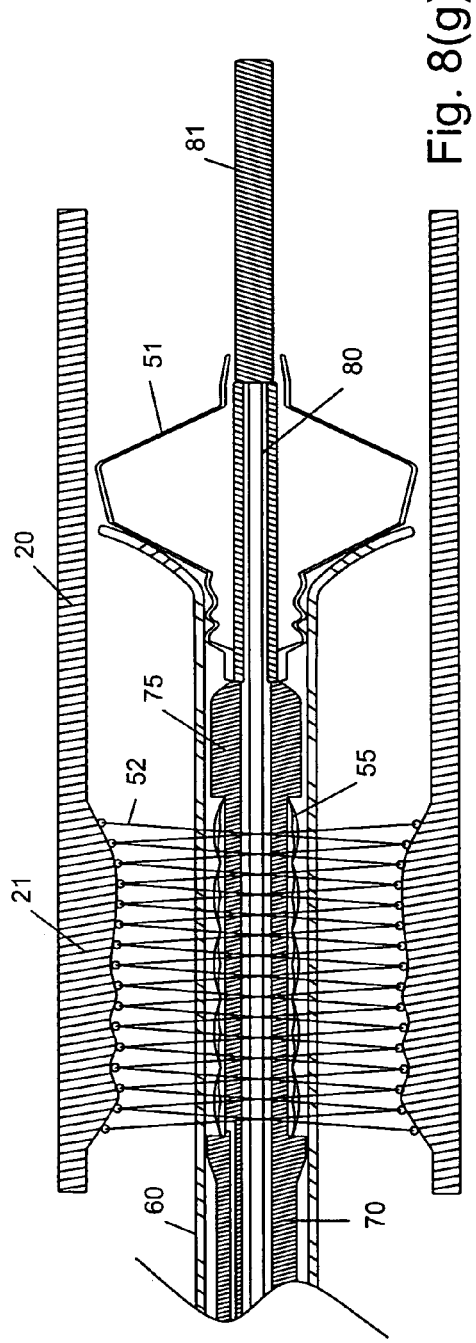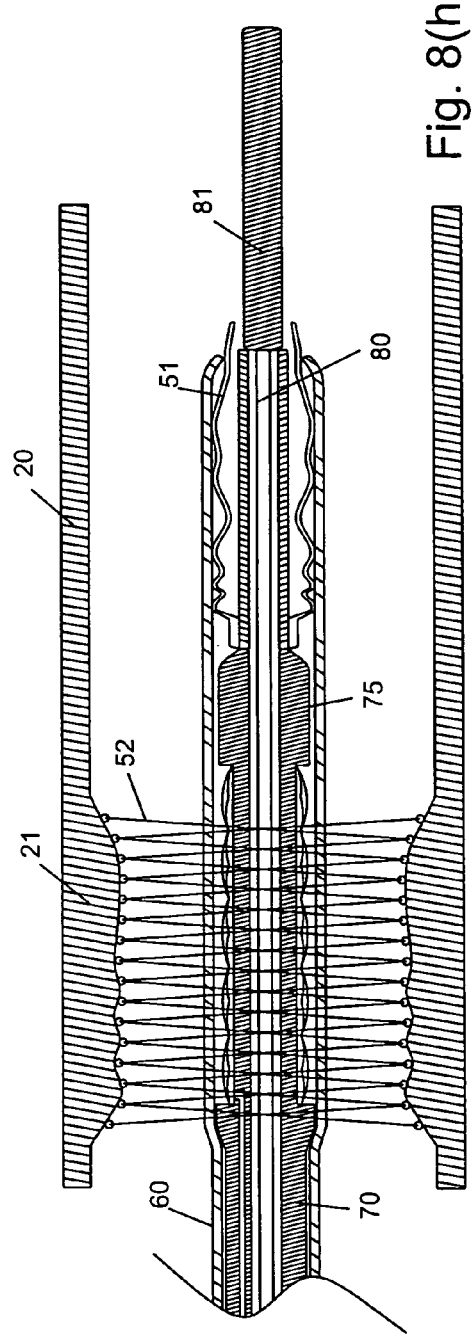

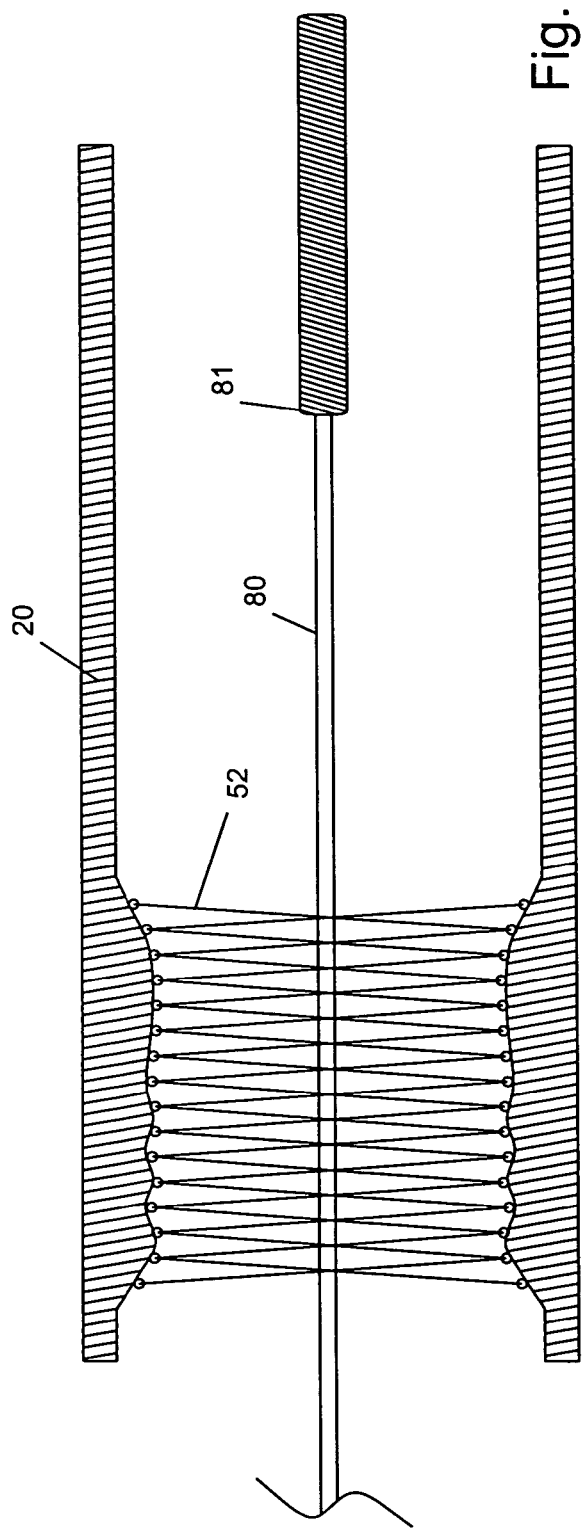

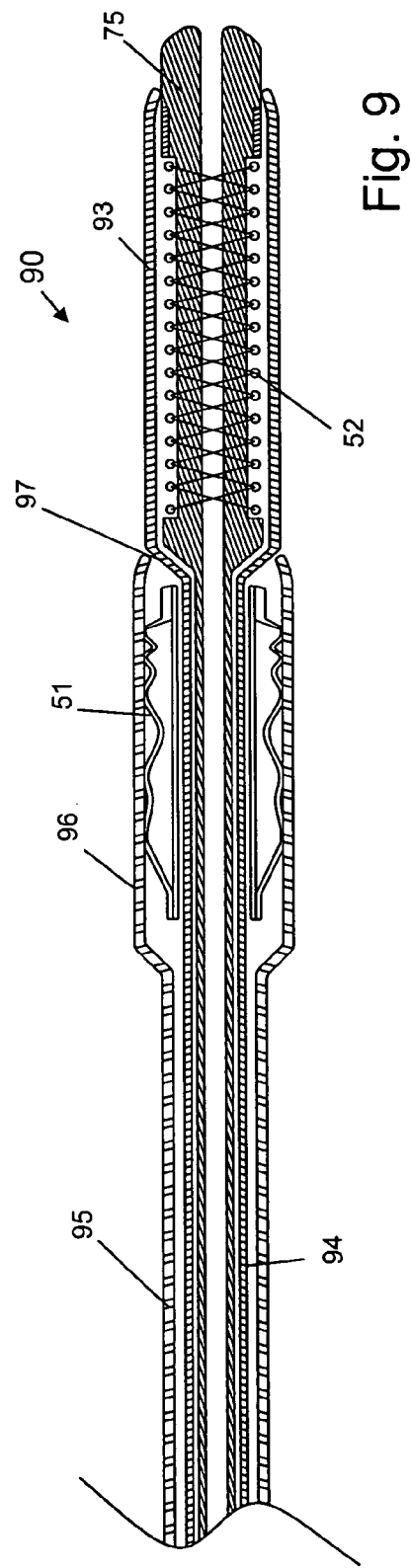

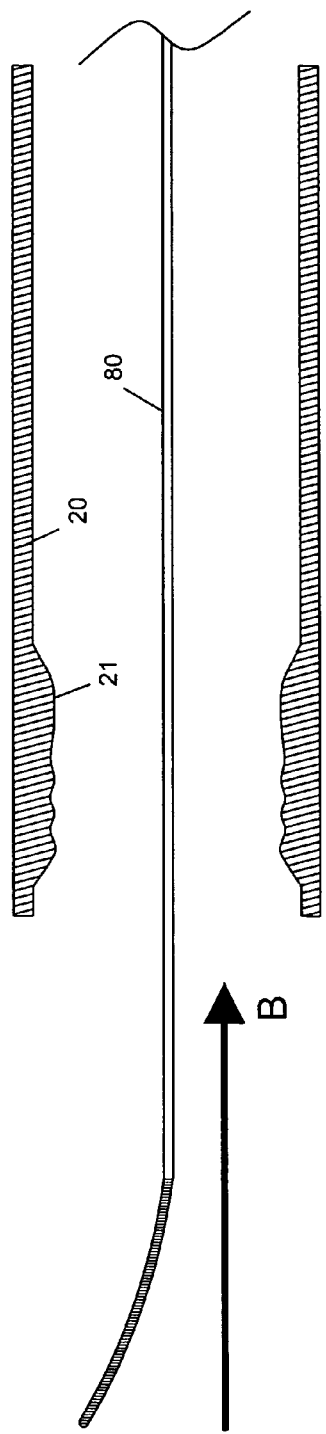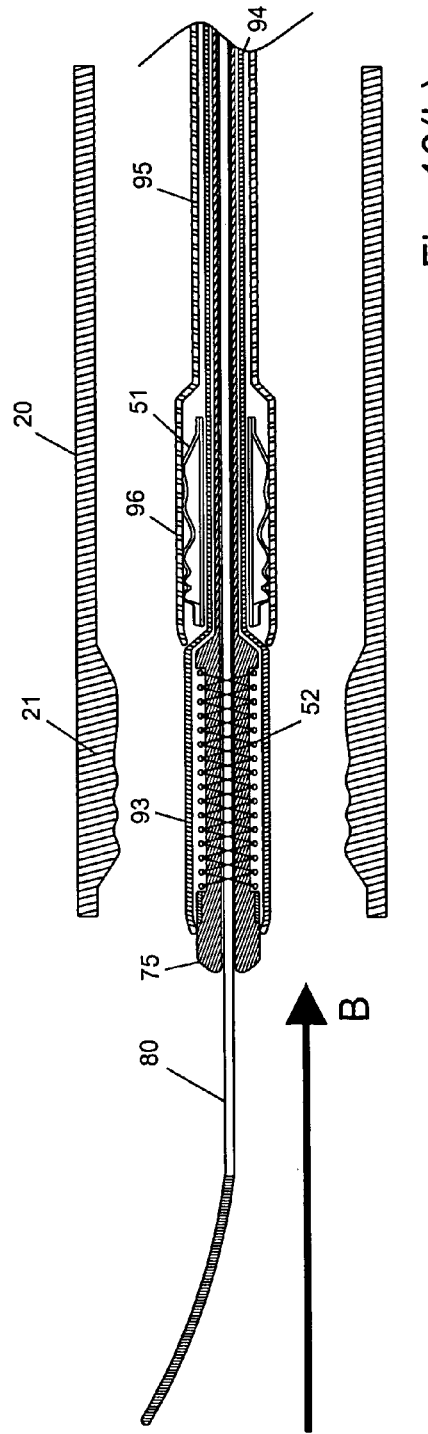

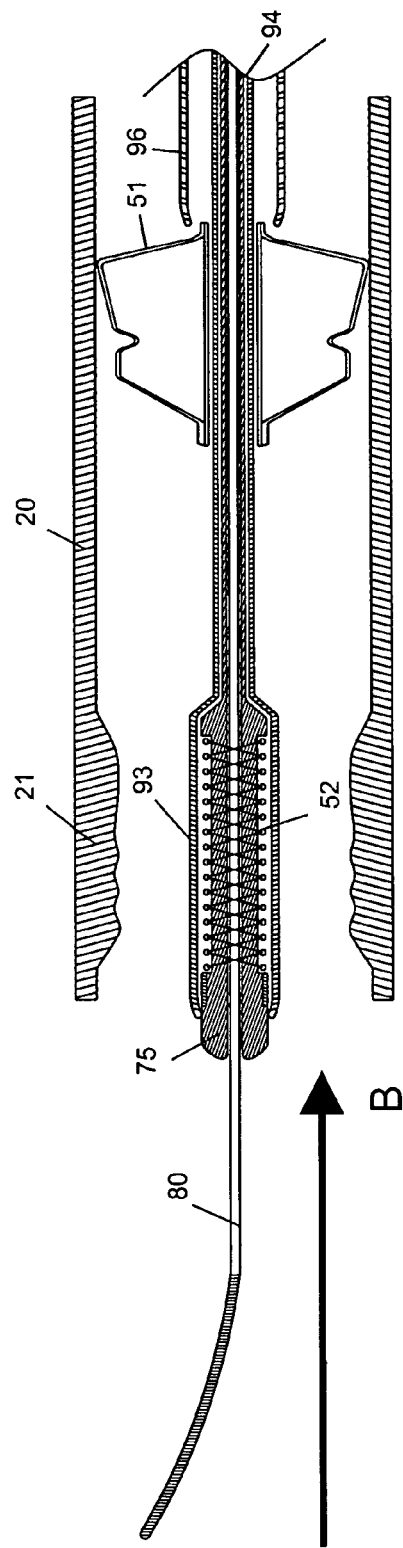
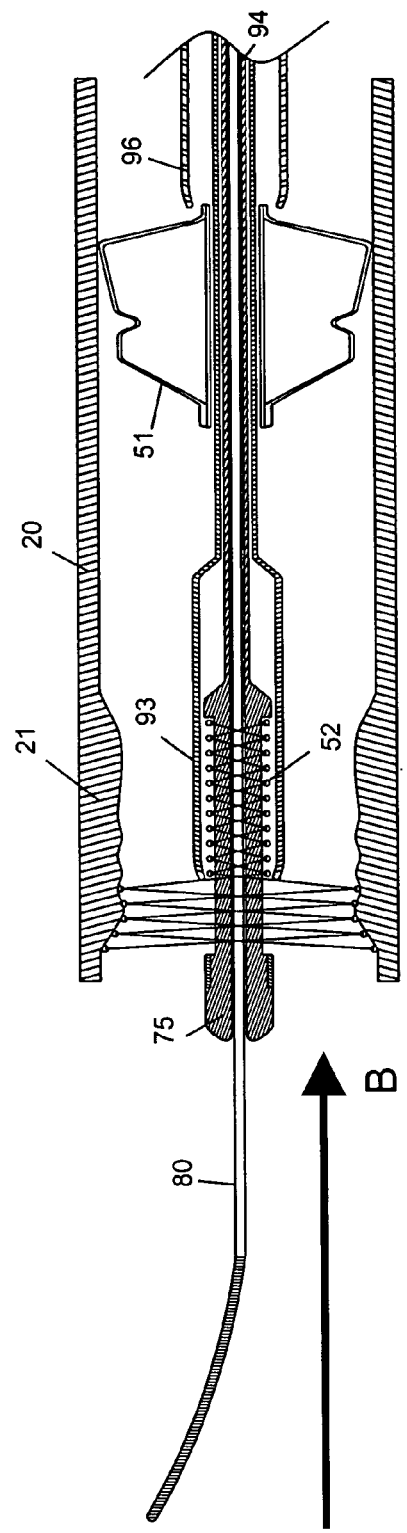
Fig. 10(c)
Fig. 10(d)

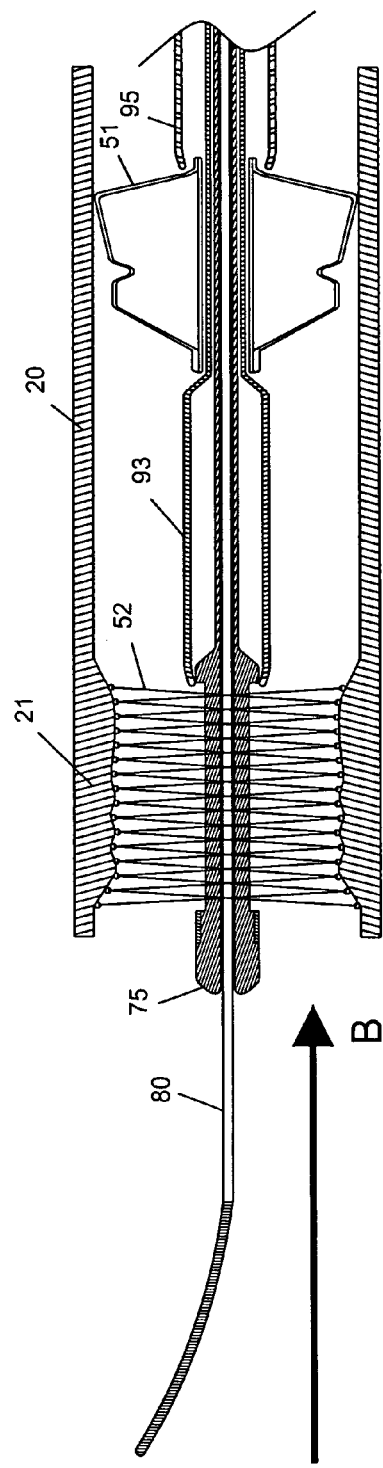
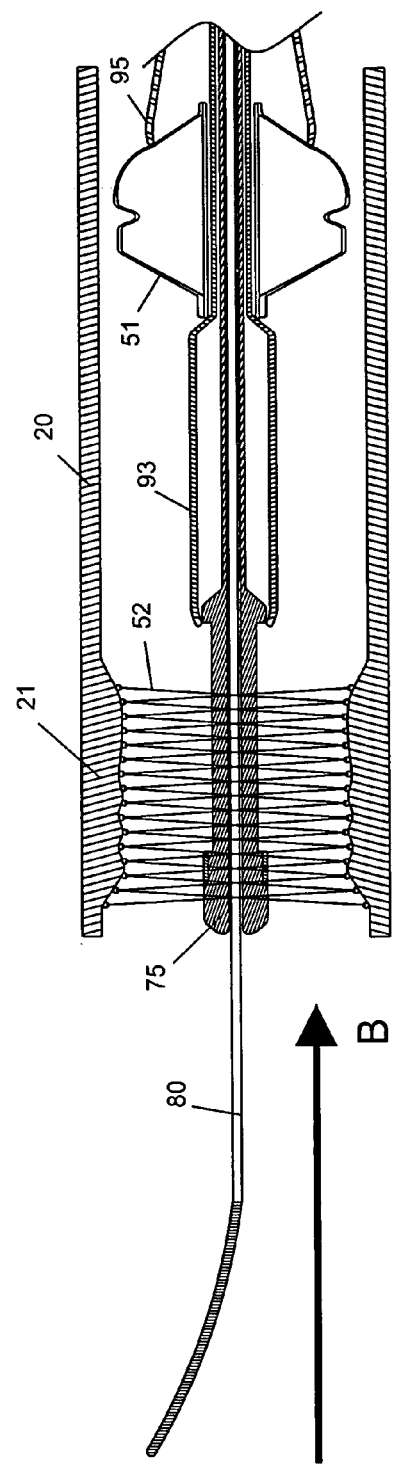
Fig. 10(e)
Fig. 10(f)

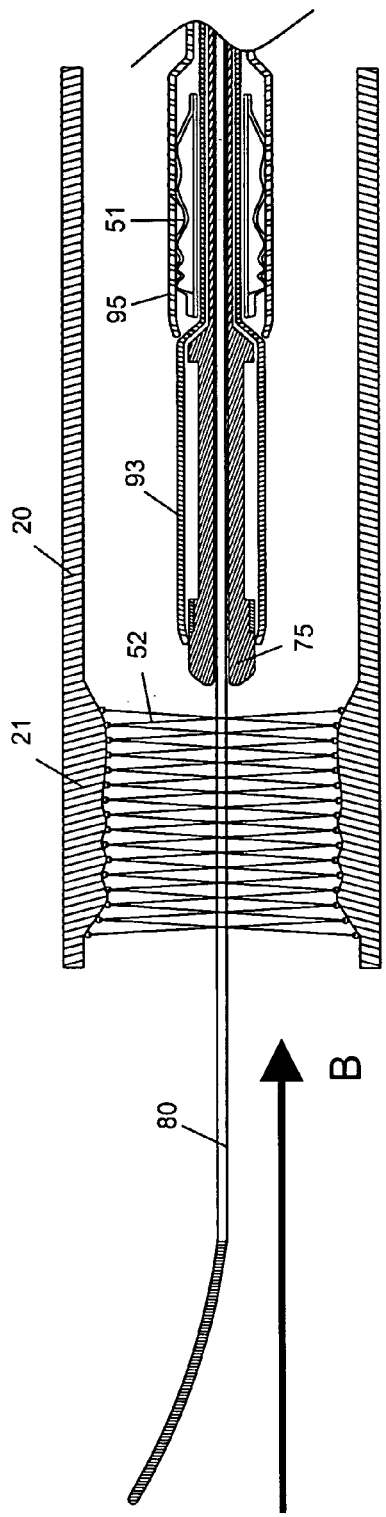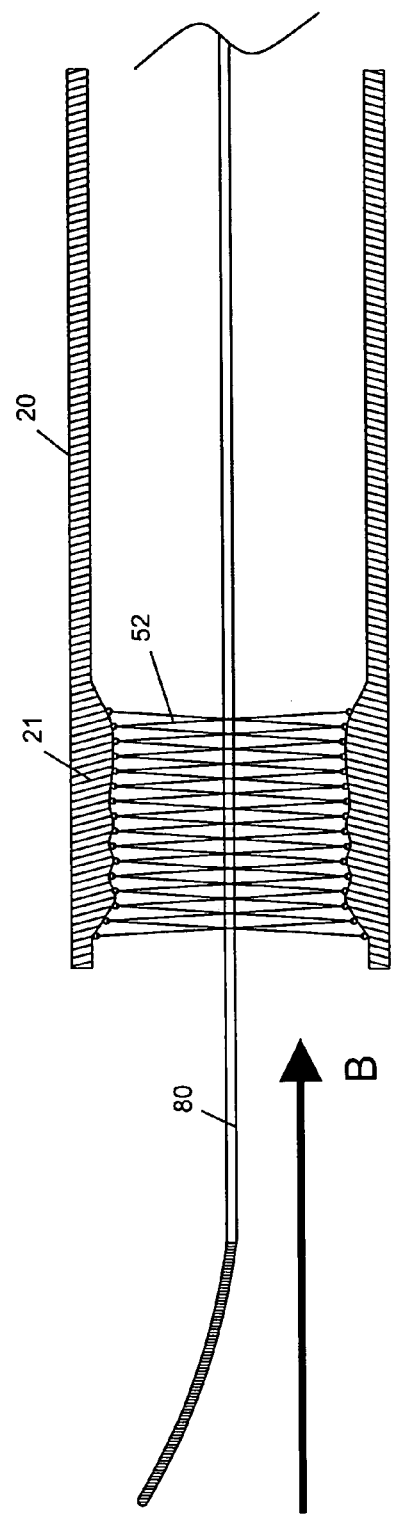

EMBOLIC PROTECTION SYSTEM

CROSS REFERENCE TO RELATED APPLICATIONS

This application claims the benefit of U.S. Provisional Application Nos. 60/379,396 filed May 13, 2002; and 60/412,545, filed Sep. 23, 2002, the contents of both of which are incorporated herein by reference.

INTRODUCTION

This invention relates to a catheter, in particular to a catheter for transporting an embolic protection filter through a vasculature.

During an interventional procedure, it is known to deploy an embolic protection filter distally of a treatment site in a vasculature using a delivery catheter. The filter is used to capture any embolic material generated during a treatment procedure subsequently performed at the treatment site. After completion of the treatment procedure the filter and the captured embolic material are retrieved from the vasculature using a retrieval catheter.

This invention is aimed at providing a catheter which enables an interventional procedure of this type to be carried out with greater safety and more efficiently.

This invention also relates to a delivery and deployment catheter system for medical devices and in particular to an integrated catheter system for delivery and sequential deployment of a filter and treatment of a vasculature, for example by deployment of a stent, at desired locations in a vasculature.

Vascular filters are used in conjunction with a stent during interventional procedures, such as the treatment of carotid artery stenosis. In particular it is known to provide a stent and a filter mounted together on a single guidewire. WO 98/47447 describes a system of this type in which the stent is balloon expandable. WO 98/50103 describes a similar system in which the stent is self-expanding.

An integrated system which includes both a stent and a filter has the advantage that the deployment procedure is, in theory, simpler and quicker as a single deployment catheter can be used. However, in clinical practice the site to be treated is often difficult to access and the space available for deployment of a distal filter is severely restricted. For example, in carotid arteries the distance distal to the stenosed area may be limited. Thus, in a number of cases conventional integrated devices cannot be used.

There is therefore a need for an improved integrated system which has the advantage of a treatment device, such as a stent, and a filter carried on a single catheter but which also facilitates practical implementation at almost any desired site in the vasculature.

STATEMENTS OF INVENTION

According to the invention, there is provided a catheter having an internal reception space for receiving an embolic protection filter for transporting the filter through a vasculature; and
the catheter comprising means to facilitate treatment of a site in a vasculature.

The catheter of the invention has the dual functions of transporting an embolic protection filter through a vasculature, and providing the means to facilitate treatment of the vasculature. This enables an interventional procedure to be carried out without requiring the treatment site to be crossed as many times as in conventional interventional procedures, which will reduce the risk of dislodging emboli or damaging the vessel.

For example, when the catheter is a delivery catheter, the treatment site only has to be crossed once to enable deployment of an embolic protection filter, and to enable a treatment procedure to be performed at the treatment site.

When the catheter is a retrieval catheter, the treatment site only has to be crossed once to enable a treatment procedure to be performed at the treatment site, and to enable retrieval of an embolic protection filter.

When the catheter acts as both a delivery catheter and a retrieval catheter, the treatment site only has to be crossed once to enable deployment of an embolic protection filter, to enable a treatment procedure to be performed at the treatment site, and to enable retrieval of the filter.

By minimising the number of times that the treatment site has to be crossed during the interventional procedure, the possibility of embolic material being released from the treatment site during a crossing step is minimised. In addition, the overall interventional procedure will be a more efficient one, and may be performed more quickly.

In one embodiment of the invention the catheter comprises a delivery catheter. Preferably the catheter has an outer tubular body and an inner member extending at least partially through the outer body, the inner member being movable distally relative to the outer body to deploy an embolic protection filter from within the reception space.

In another embodiment of the invention the catheter comprises a retrieval catheter. Preferably the catheter has an outer tubular body and an inner member extending at least partially through the outer body, the inner member being movable proximally relative to the outer body from an introduction configuration to a retrieval configuration to facilitate retrieval of an embolic protection filter into the reception space. Ideally in the introduction configuration, the inner member protrudes from a distal end of the outer body. Most preferably a distal tip of the inner member tapers distally inwardly. The inner member may be at least partially inflatable.

In one case the catheter defines a guidewire lumen extending at least partially therethrough for passing the catheter over a guidewire. The guidewire lumen may extend only partially through the catheter to facilitate passing the catheter over a guidewire in a rapid exchange manner.

In a preferred embodiment the means to facilitate treatment is at least partially provided on the inner member. Ideally in the introduction configuration, the means to facilitate treatment protrudes from a distal end of the outer body.

In another embodiment the means to facilitate treatment is at least partially provided on the outer tubular body. Preferably the means to facilitate treatment is provided at a necked down portion of the outer tubular body. Ideally the catheter comprises a cover around the means to facilitate treatment in the introduction configuration. The cover may be moveable proximally to uncover the means to facilitate treatment. Most preferably the cover comprises a sheath. In one case the sheath extends along the full length of the outer tubular body. Ideally a distal end of the sheath tapers distally inwardly.

In a further embodiment of the invention the outer tubular body extends along substantially the full length of the inner member.

In one case the means to facilitate treatment comprises an angioplasty balloon.

In another case the means to facilitate treatment comprises a stent deployment balloon.

In a further case the means to facilitate treatment comprises a sheath movable from a delivery configuration, in which a treatment device is restrainable by the sheath in a collapsed configuration, to a deployment configuration, in which the treatment device is uncovered. Ideally the treatment device is a self-expanding stent. The sheath may be provided by the outer body.

In a further aspect, the invention provides a treatment apparatus comprising:— a catheter of the invention and a treatment device.

In a preferred embodiment the treatment device is a self-expanding stent.

In another aspect of the invention, there is provided a method for the capture and removal of embolic material from a vasculature during an interventional procedure comprising the steps of:— introducing a delivery catheter into a vasculature, the delivery catheter having an embolic protection filter received within the catheter;

advancing the delivery catheter through the vasculature to cross a desired treatment site in the vasculature;

deploying the filter out of the delivery catheter at a deployment site distally of the treatment site;

carrying out a treatment procedure at the treatment site in the vasculature, embolic material generated during the treatment procedure being captured by the filter;

advancing a retrieval catheter through the vasculature to cross the treatment site;

retrieving the filter into the retrieval catheter; and withdrawing the retrieval catheter and the retrieved filter from the vasculature;

wherein the treatment procedure is at least partially carried out using the delivery catheter after deployment of the filter.

The treatment procedure may be at least partially carried out using the retrieval catheter before retrieving the filter into the retrieval catheter.

The invention provides in a further aspect a method for the capture and removal of embolic material from a vasculature during an interventional procedure comprising the steps of:— introducing a delivery catheter into a vasculature, the delivery catheter having an embolic protection filter received within the catheter;

advancing the delivery catheter through the vasculature to cross a desired treatment site in the vasculature;

deploying the filter out of the delivery catheter at a deployment site distally of the treatment site;

carrying out a treatment procedure at the treatment site in the vasculature, embolic material generated during the treatment procedure being captured by the filter;

advancing a retrieval catheter through the vasculature to cross the treatment site;

retrieving the filter into the retrieval catheter; and withdrawing the retrieval catheter and the retrieved filter from the vasculature;

wherein the treatment procedure is at least partially carried out using the retrieval catheter before retrieving the filter into the retrieval catheter.

The filter may be delivered and retrieved using a single medical catheter.

In one case the medical catheter remains in the vasculature throughout the interventional procedure.

The treatment procedure may comprise a balloon angioplasty procedure. The treatment procedure may comprise a stent deployment procedure. In one case the stent is self-expanding. In another case the stent is expanded by inflation of a balloon.

In another aspect of the invention, there is provided a transportation device comprising a reception portion having a reception space for receiving a medical device, and a control tether extending proximally of the reception portion to facilitate control of the position of the reception portion.

The reception portion preferably comprises a tubular sheath.

In a further aspect of the invention there is provided a catheter assembly comprising a transportation device of the invention and a catheter extendable through the reception space, the catheter being movable proximally relative to the reception space to facilitate reception of a medical device within the reception space.

According to the invention there is provided a delivery and deployment catheter system comprising:— a filter catheter section;

a filter mounted in the filter catheter section, the filter being movable on release from the filter catheter section from a collapsed delivery configuration to an expanded deployment configuration;

a stent catheter section;

a stent mounted in the stent catheter section, the stent being movable on release from the stent catheter section from a retracted delivery configuration to an expanded deployment configuration; and a guidewire extending through the catheter sections;

the stent catheter section and associated stent being movable along the guidewire independently of the deployed filter for sequential deployment of the filter and stent.

In one embodiment of the invention the catheter system includes at least one stop for limiting longitudinal movement of the filter and/or the stent relative to the guidewire.

The stop may be a filter stop for limiting movement of the filter in the proximal direction.

The stop may be a stent stop for limiting movement of the stent in the proximal direction.

In a preferred embodiment of the invention the stent catheter section is located proximal to the filter catheter section.

Preferably an outer sheath comprises the filter catheter section and the stent catheter section. Ideally an inner tube extends axially through the outer sheath.

Desirably the guidewire extends through the inner tube.

Preferably a distal end of the inner tube provides a proximal stop for the filter.

The inner tube may have an abutment to provide a proximal stop for the stent.

In an alternative preferred embodiment of the invention the stent catheter section is located distal to the filter catheter section. Ideally the stent catheter section comprises an outer stent retaining sheath for the stent and the filter catheter section comprises an outer filter retaining sheath for the filter.

A first ring may be mounted on the guidewire intermediate the stent and the filter to provide a proximal stop for the stent. A second ring may be mounted on the stent retaining sheath proximal of the filter to provide a proximal stop for the filter.

In a preferred embodiment of the invention the filter has a carrier with a guide olive mounted at the distal end thereof, the guide olive being configured to engage with the distal end of the catheter section in the collapsed configuration of the filter body to provide a smooth transition between the catheter section and the guidewire tip.

In one embodiment of the invention the filter has a proximal and a distal end, inlet openings being positioned at the proximal end and outlet holes being positioned at the distal end.

In an alternative embodiment of the invention the filter has a proximal and a distal end, inlet openings being positioned at the distal end and outlet holes being positioned at the proximal end.

Ideally the filter is a self-expanding filter.

The stent may be a self-expanding stent. Alternatively the stent may be a balloon expandable stent.

In another aspect the invention provides a method for delivery and deployment of a filter and a stent in a vasculature comprising the steps of:— providing a catheter system comprising a filter catheter section housing a filter, a stent catheter section housing a stent, and a guidewire extending through the catheter sections;

advancing the catheter system through the vasculature so that the filter catheter section and the stent catheter sections are located approximately in a desired treatment region;

advancing the filter catheter section to a desired filter location;

deploying the filter from the filter catheter section;

moving the stent catheter section independently of the filter to a desired stent location; and deploying the stent from the stent catheter section.

In one embodiment of the invention the stent is deployed by retracting the stent catheter section to uncover the stent.

In another embodiment of the invention the filter is deployed by retracting the filter catheter section to uncover the filter.

Preferably the stent and the filter are deployed by retracting a single catheter comprising the stent catheter section and the filter catheter section.

In a preferred embodiment of the invention the method includes the step of limiting movement of the stent in the proximal direction.

In a further embodiment of the invention the method includes the step of limiting movement of the filter in the proximal direction.

The invention also provides a catheter system comprising a filter delivery catheter and a treatment device delivery catheter, the filter delivery catheter comprising a filter retaining sheath and a shaft extending from the sheath, the treatment device delivery catheter comprising a treatment device retaining sheath and a shaft extending from the sheath, the treatment device delivery catheter shaft being extendable through the filter delivery catheter. The treatment device may be a stent.

In another aspect the invention provides a method for carrying out a procedure at a treatment site in a vasculature comprising the steps of:— providing an embolic protection device;

deploying the embolic protection device distal of the treatment site;

providing a procedural catheter comprising a tubular member having a distal space housing a medical device;

advancing the procedural catheter to the treatment site;

deploying the medical device from the procedural catheter at the treatment site; and retrieving the embolic protection device into the procedural catheter.

In one embodiment of the invention the medical device is a stent;

the procedural catheter is a stent delivery catheter having a distal reception space housing a stent; and the method comprises deploying the stent from the stent delivery catheter; and retrieving the embolic protection device at least partially into the reception space in the stent delivery catheter.

The stent may be a self expanding stent or a balloon expandable stent.

In one case the procedural catheter comprises a balloon catheter and the method comprises deploying the balloon at the treatment site.

The balloon may be a post dilitation balloon and/or a stent expanding balloon.

In one embodiment the embolic protection device is retrieved into the procedural catheter by engaging the embolic protection device.

Preferably the procedural catheter has an inner member. The inner member may comprise a centering member which projects distally of the distal end of the procedural catheter.

The inner member may comprise an engagement element for engagement with an embolic protection device.

The method may comprise advancing a guidewire through the vasculature so that a distal tip of the guidewire is located distal of the treatment location, and then advancing the catheter over the guidewire. The guidewire may have a distal stop and the embolic protection device is retrieved by engaging the distal stop of the guidewire with the embolic protection device.

In another aspect the invention provides a method for carrying out a procedure at a treatment site in a vasculature comprising the steps of:— providing a catheter comprising a tubular member having a distal space, the distal space comprising a first portion and a second portion, the first portion being adjacent to and distal of the second portion;

providing a treatment device loaded into the second portion of the distal space of the catheter;

providing an embolic protection device loaded into the first portion of the distal space of the catheter; the embolic protection device having a collapsed configuration for transport through the vasculature and an expanded deployed configuration for collecting emboli released during a procedure;

advancing the catheter to a treatment site in the vasculature;

deploying the embolic protection device from the first portion of the distal space in the catheter, the deployed filter taking up an expanded emboli-collecting configuration distal to the treatment location; and deploying the treatment device from the second portion of the distal space in the catheter to carry out a procedure at the treatment site.

In one embodiment the method comprises retrieving the embolic protection device into the reception space of the catheter after completion of the procedure.

In one embodiment the method comprises advancing a guidewire through the vasculature so that a distal tip of the guidewire is located distal of the treatment location, and then advancing the catheter over the guidewire.

The treatment device may comprise a balloon such as an angioplasty balloon.

The treatment device may comprise a stent such as a self expanding stent or a balloon expandable stent.

In one embodiment the treatment device is mounted on an inner member. The embolic protection device may be engaged with the inner member to deploy the embolic protection device.

The inner member may define a centring member.

The invention further comprises a method for carrying out a procedure at a treatment site in a vasculature comprising the steps of:— providing a catheter system comprising a filter delivery catheter and a treatment device delivery catheter, the filter delivery catheter comprising a filter retaining sheath and a shaft extending from the sheath, the treatment device delivery catheter comprising a treatment device retaining sheath and a shaft extending from the sheath, the treatment device delivery catheter shaft extending through the filter delivery catheter sheath and shaft;

providing a treatment device loaded into the treatment device delivery sheath;

providing an embolic protection device loaded into the filter sheath, the embolic protection device having a collapsed configuration for transport through the vasculature and an expanded deployed configuration for collecting emboli released curing a procedure;

advancing the catheter system to a treatment site in the vasculature;

deploying the embolic protection device from the filter sheath, the deployed filter taking up an expanded emboli-collecting configuration; and deploying the treatment device from the sheath of the treatment device delivery catheter.

In one embodiment the method comprises retrieving the embolic protection device into the reception space of the catheter after completion of the procedure.

In one embodiment the method comprises advancing a guidewire through the vasculature so that a distal tip of the guidewire is located distal of the treatment location, and then advancing the catheter over the guidewire.

The treatment device may comprise a balloon such as an angioplasty balloon.

The treatment device may comprise a stent such as a self expanding stent or a balloon expandable stent.

The treatment device may be mounted on an inner member.

The embolic protection device may be-engaged with the inner member to deploy the embolic protection device.

BRIEF DESCRIPTION OF THE DRAWINGS

The invention will be more clearly understood from the following description of some embodiments thereof, given by way of example only, with reference to the accompanying drawings, in which:—

FIG. 1 is a cross sectional view of a distal section of a catheter according to the invention;

FIGS. 2(a) to 2(i) are schematic cross sectional views illustrating various steps in a vascular interventional procedure using the catheter of FIG. 1;

FIG. 3 is a cross sectional view of a distal section of another catheter of the invention;

FIGS. 4(a) to 4(i) are schematic cross section views illustrating various steps in a vascular interventional procedure using the catheter of FIG. 3;

FIG. 5 is a cross sectional view of a distal section of another catheter according to the invention;

FIG. 6 is a cross sectional view of a distal section of a further catheter of the invention;

FIG. 7 is a cross sectional view of a distal section of another catheter of the invention;

FIGS. 8(a) to 8(i) are schematic cross sectional views illustrating various steps in a vascular interventional procedure using the catheter of FIG. 7;

FIG. 9 is a cross sectional view of a distal section of a further catheter system of the invention; and FIGS. 10(a) to 10(h) are schematic cross sectional views illustrating various steps in a vascular interventional procedure using the catheter of FIG. 9.

DETAILED DESCRIPTION

Figure 4I:
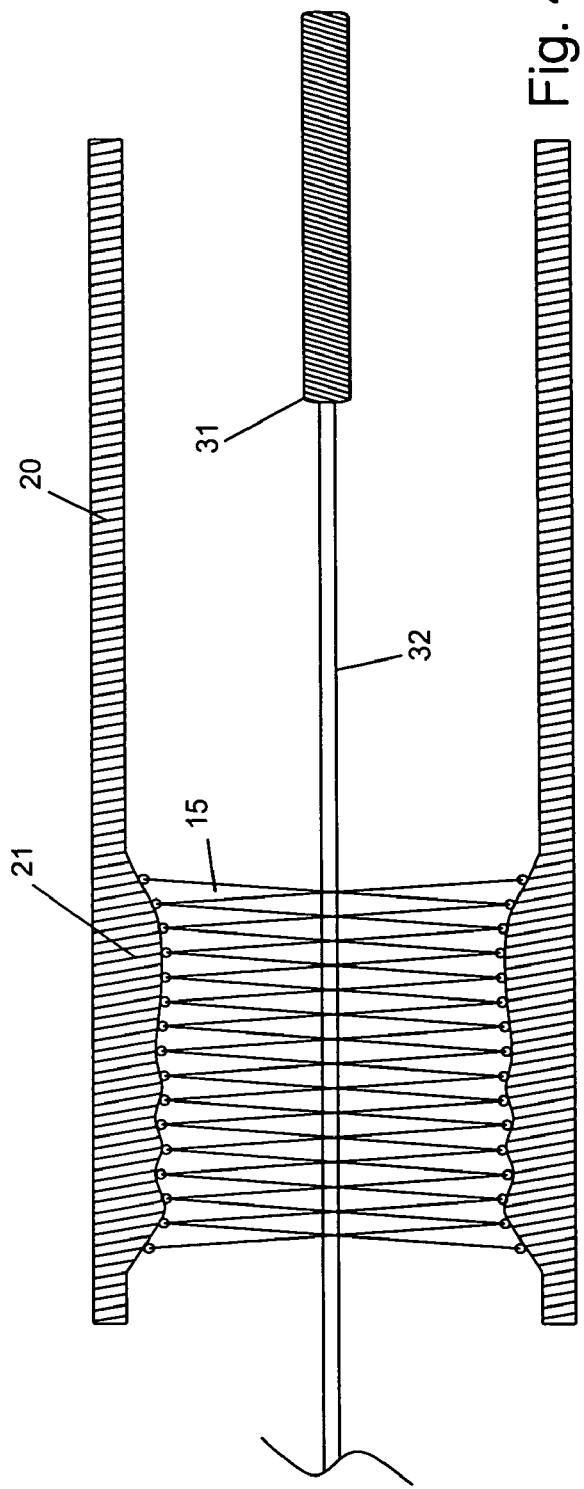

Referring to the drawings there is illustrated a catheter according to the invention. The catheter has an internal reception space for receiving an embolic protection filter to enable the filter to be transported through a vasculature, and the catheter comprises means to facilitate treatment of a site in the vasculature.

The catheters of the invention facilitate carrying our at least two procedures using a single catheter. In some cases the catheter facilitates delivery of an embolic protection device distal to a treatment location and carrying out a procedure at the treatment site such as an angioplasty or deployment of a stent. In other cases the catheter facilitates carrying out of a procedure at the treatment site such as an angioplasty or a stent deployment and subsequent retrieval of the embolic protection device into the same catheter completion of the procedure.

The embolic protection device may comprise a filter such as those described in International patent applications Nos. PCT/IE00/00053 (U.S. Ser. No. 09/985,820), and/or PCT/IE00/00054 (U.S. Ser. No. 09/986,132), and/or PCT/IE00/00055 (U.S. Ser. No. 09/986,064), and/or PCT/IE98/00093 (U.S. Ser. No. 09/188,472), the relevant contents of which are incorporated herein by reference.

Referring initially to FIGS. 1 and 2(a) to 2(i) a catheter 1 has an outer tubular body 3, and an inner member 4 extending through the entire length of the outer body 3. The outer body 3 has an expandable distal tip 5 to facilitate retrieval of a filter 10 into the outer body 3.

The inner member 4 is movable relative to the outer body 3 from an introduction configuration (FIGS. 1 and 2(c)) to a treatment device deployment configuration (FIGS. 2(d) to 2(f)) to a retrieval configuration FIGS. 2(g) and 2(h) to facilitate retrieval of the filter 10 into an internal reception space 11 of the catheter 1.

In the introduction configuration, the inner member 4 protrudes distally from the distal tip 5 of the outer body 3 to ensure that the outer body 3 does not snag during advancement of the catheter 1. As illustrated in FIG. 1, a distal tip 6 of the inner member 4 tapers distally inwardly to provide a smooth crossing profile for the catheter 1 in the introduction configuration.

The catheter 1 has a guidewire lumen 2 which may extend through the entire length of the inner member 4 for passing the catheter 1 over a guidewire 12. The inner member 4 assists in centring the catheter 1 around the guidewire 12 during advancement of the catheter 1 through a vasculature 20 to a treatment site such as a region 21 of stenosis.

In this case, the treatment device is provided by a stent 15 carried by the inner member 4 as illustrated in FIG. 1. The stent 15 is in this case expandable by a balloon 16 through an inflation lumen 17 defined in the inner member 4.

The stent 15 and balloon 16 are mounted on a stepped down section 4A of the inner member distal of the intermediate member 18. Marker bands 19 on the section 4A assist in visualisation during stent positioning and deployment.

In use, an embolic protection filter 10 is collapsed down and loaded into a reception space of a delivery catheter, in a manner similar to that described in International patent application No. PCT/IE01/00052 (U.S. Ser. No. 09/838,544), the relevant contents of which are incorporated herein by reference.

The delivery catheter is then introduced into a vasculature and advanced through the vasculature over a guidewire 12 to cross a desired treatment site 21 in the vasculature 20. The filter 10 is deployed out of the delivery catheter at a deployment site distally of the treatment site, and the delivery catheter is withdrawn from the vasculature.

An initial angioplasty procedure may be carried out at the treatment site 21 using a conventional angioplasty balloon 29.

The retrieval catheter 1 is then introduced into the vasculature, and advanced through the vasculature over the guidewire 12 in the introduction configuration with the tapered tip 6 protruding distally from the distal tip 5 of the outer body 3. During advancement, the stent 15 and balloon 16 are in a low-profile, deflated configuration surrounded by the outer body 3, as illustrated in FIG. 1. The outer body 3 assists in restraining the deflated balloon 16 to minimise the overall crossing profile of the catheter 1.

When the retrieval catheter 1 is correctly positioned at the treatment site the stent 15 is deployed. In this case, to deploy the stent the sheath 3 is retracted relative to the shaft 4 and the balloon 16 is inflated to expand the stent 15 at the region of stenosis 21 [FIGS. 2(e) and 2(f)]. The balloon 16 is inflated by passing an inflation fluid through the inflation lumen 17 from the proximal end of shaft 4.

In this manner a stenting treatment procedure is carried out at the treatment site. Any embolic material generated during the treatment procedure is captured by the deployed filter 10.

After completion of the treatment procedure, the balloon 16 is deflated, and the outer body 3 is advanced over the deflated balloon 16 and the inner member 4 until the distal end 5 of the sheath 3 is immediately proximal of the deployed filter 10. In this case the distal tip 6 of the inner member 4 is engaged with the filter 10 to facilitate retrieval. It will be noted that the distal tip 6 has gripping formations 25 which engage with corresponding gripping formations on the filter 26. After engagement of the filter 10 the inner member 4 is moved proximally, relative to the sheath 3, thus capturing the filter 10 as illustrated in FIGS. 2(g) and 2(h). Any embolic material captured by the filter 10 is safely retained within the filter 10 during retrieval. The catheter 1 with the retrieved filter 10 may then be removed from the vasculature. The guidewire 12 may be removed with the catheter 1 or may be left in place [FIG. 2(i)]

Referring to FIGS. 3 and 4(a) to 4(i) another catheter 30 is illustrated which is similar to the catheter of FIGS. 1 and 2 and like parts are assigned the same reference numerals. In this case the embolic protection filter 10 is retrieved using a distal stop 31 on the guidewire 32. The guidewire 32 is then retracted to engage a distal stop 31 on the guidewire 32 with the filter 10 (FIGS. 4(j) and 4(h)), in a manner similar to that described in International patent application No. PCT/IE01/00053 (U.S. Ser. No. 09/985,820), the relevant contents of which are incorporated herein by reference.

By retracting the guidewire 32 while maintaining the position of the outer body 3, the filter 10 is collapsed down and retrieved into the reception space in the distal tip 5 of the outer body 3 (FIGS. 4(g) and 4(h)). Any embolic material captured by the filter 10 is safely retained within the filter 10 during this retrieval step.

The retrieval catheter 1 and the retrieved filter 10 are then withdrawn from the vasculature, as illustrated in FIG. 4(h). In this way any embolic material retrieved during the interventional procedure is safely captured and removed from the vasculature.

Referring to FIG. 5 there is illustrated another catheter system 40 which is similar to these described above and like parts are assigned the same reference numerals. In this case the distal tip 6 of the inner member 4 is partially located inside the outer body 3 in the delivery mode.

Referring to FIG. 6 there is illustrated a further catheter system 45 which is again similar to these described above and like parts are assigned the same reference numerals. In this case the distal tip 6 of the inner member 4 is located outside the outer body 2.

In all cases the guidewire lumen 2 may extend only partially through the catheter. This arrangement enables the catheter to be passed over a guidewire in a rapid exchange manner. To facilitate rapid exchange, the inner member 4 may also extend only partially through the outer body 3.

It will be appreciated that the treatment procedure may involve several steps, such as a primary deployment of a stent at the treatment site followed by a post-stenting dilation of the treatment site.

The catheter of the invention may also be used as a delivery catheter to deliver an embolic protection filter to a desired deployment site in a vasculature. In this case, the delivery catheter has an outer tubular body and an inner member extending through the entire length of the outer body. The inner member is movable distally relative to the outer body to deploy the embolic protection filter from within the reception space of the catheter to the deployment site in the vasculature.

After deployment of the filter, the delivery catheter may be used to carry out the treatment procedure at the treatment site.

It will be appreciated that the same medical catheter may be used to deliver the filter, perform the treatment procedure, and retrieve the filter. In this case, the catheter may remain in the vasculature throughout the interventional procedure.

Referring to FIGS. 7 and 8(a) to 8(i) there is illustrated a catheter system 50 according to the invention for delivery and deployment of a filter 51 and a stent 52. The catheter system 50 can also be used to retrieve the filter after stenting. The catheter system comprises an outer catheter 60 with a distal sheath 61 which is pulled back to deploy the filter 51 and an inner stent delivery member 70 which extends axially through the outer catheter 60. The inner stent delivery catheter 70 and the filter 51 are slidable over a guidewire 80 which in this case has a distal stop 81.

The catheter system may be of an over the wire or a rapid exchange configuration. The guidewire 80 has a soft tip at its distal end to assist in navigation of the guidewire 80 through a vascular system 20 to a position that is distal to a treatment location such as a region 21 of stenosis.

Axial movement of the filter 51 along the guidewire 80 is limited by a distal end 75 of the inner member 70 which acts as a proximal stop for the filter 51. The filter 51 is radially self expandable between a collapsed stored position to an expanded position extending outwardly of the guidewire 80 on deployment in the vasculature 20.

The filter 51 may comprise a polymeric membrane mounted over a collapsible support frame. The support frame is such that in use it expands and can be collapsed inwardly for loading in the sheath 61 or the like. The membrane has large inlet openings and small outlet openings. The inlet openings allow blood and embolic material to enter the filter. The outlet openings allow through passage of blood but retain undesired embolic material within the filter. The filter is oriented such that the inlet openings are at the proximal end of the filter and the outlet openings are at the distal end of the filter. Such filters are described in our WO-A-99/23976 (U.S. Ser. No. 09/188,472), the entire contents of which are incorporated herein by reference. However any other suitable filter may be used in the catheter systems and procedures of this invention.

The stent 52 is housed between the sheath 61 and the inner stent delivery catheter 70. Proximal movement of the stent 52 is limited by a shoulder 74 formed on the inner member 70. The stent 52 may be a self-expanding stent of a shape memory material, such as Nitinol. One such stent is described in U.S. Pat. No. 5,827,321. Alternatively or additionally the stent may be expanded by a balloon 55.

A delivery configuration of the catheter system is illustrated in FIG. 7, in which the sheath 61 encloses both the stent 52 and the filter 51. In use, the catheter system 50 is advanced in the delivery configuration through the vasculature 20 until the filter 51 is at a desired filter location, for example distal to a region of stenosis 21 in the vasculature 20, as illustrated in FIG. 8(b). The sheath 61 is retracted a limited distance to uncover the filter 51 and thereby enable it to be deployed, as illustrated in FIG. 6(c). The filter 51 may be deployed by engaging a distal tip 75 of the inner member 70 with the collapsed filter 51.

The sheath 61, the stent 52 and the inner member 70 are then moved axially until the stent 52 is at a desired stent location, for example at the region of stenosis 21. The sheath 61 is further retracted to uncover the stent 52, thereby enabling the stent 51 to be deployed as illustrated in FIGS. 8(d) and 8(e). The balloon 55 is then inflated to further expand the stent [FIG. 8(f)]. The balloon 55 is then deflated.

After treatment of the stenosed region 21 the filter 51 may be retrieved into the catheter thereby capturing the embolic material retained therein [FIGS. 8(g) and 8(h)]. The catheter is then withdrawn with the collapsed filter 51 from the vasculature 20. The guidewire 80 may be left in place [FIG. 8(i)] or removed.

Referring to FIGS. 9 and 10(a) to 10(h) there is illustrated another catheter system 90 according to the invention, which is similar to the catheter system of FIGS. 7 and 8, and the same reference numerals are used to denote similar elements. In this case the stent 52 is mounted within a stent retaining distal sheath 93 of a stent delivery catheter 94. The filter 51 is mounted within a filter retaining distal sheath 96 of filter delivery catheter 95. The filter 52 is oriented such that the inlet openings are at the distal end and the outlet openings are at the proximal end.

A delivery configuration of the catheter system 90 is illustrated in FIG. 9, in which the stent retaining sheath 93 extends distally to enclose the stent 52. The filter retaining sheath 96 extends distally to engage a shoulder 97 formed in the stent retaining sheath 93, enclosing the filter 51, and thus providing a smooth crossing profile.

The catheter system 90 is suitable for use during an interventional procedure in which the puncture site is downstream of the treatment site and the catheter system 90 is advanced through a vasculature 20 in a direction opposite to the blood flow as indicated by the arrows B. In use the catheter system 90 is advanced in the delivery configuration through the vasculature 20 until the filter 51 is at a desired filter location, for example distal to a region of stenosis 21 in the vasculature 20, as illustrated in FIG. 10(b). The filter retaining sheath 96 is retracted to uncover the filter 51, thereby enabling the filter 51 to expand to a deployed configuration, as illustrated in FIG. 10(c).

The stent retaining sheath 93, the stent 52 are then moved until the stent 52 is at a desired stent location, for example at the region of stenosis 21. The stent retaining sheath 93 is retracted to uncover the stent 52, thereby enabling the stent 52 to expand to a deployed configuration, as illustrated in FIGS. 10(d) and 10(e). After completion of a stenting procedure the filter may be retrieved using the same catheter as illustrated in FIGS. 10(f) and 10(g). As in all the different versions of the invention, the guidewire 80 may be removed with the catheter system or may be left in place as illustrated in FIG.(h).

The invention allows a clinician to position a filter and a stent, both mounted in a single catheter independently of one another in a vasculature. This enables positioning of both the filter and the stent accurately, regardless of the particular physiology of the vasculature at the region to be treated.

The invention may be employed during surgical procedures in which a stenotic region is approached from the upstream direction or from the downstream direction.

It will be appreciated that any suitable stent may be used, for example the stent may be balloon expandable.

The distal tip of the outer body generally tapers distally inwardly towards the inner member to provide a smooth crossing profile from the inner member to the outer body by means of the tapering tip when the catheter is in the introduction configuration.

The stent receiving recess is defined between the proximal shoulder and the distal tip of the outer body. In this way, the stent is prevented from accidentally moving or deploying.

The distal tip of the outer body may be of a resilient, expansile material. This arrangement ensures that the tip tapers distally inwardly towards the inner member during advancement over the guidewire through a vasculate for a smooth crossing profile during advancement. Because the tip is expansible, the tip bends outwardly to facilitate expansion and deployment of the stent at the desired treatment site in the vasculate. After complete deployment of the stent, the resilient nature of the tip brings the tip back to the distally inwardly protruding configuration.

When it is desired to retrieve the filter into the reception space of the outer body, the inner member is moved proximally and the guidewire is retracted while maintaining the position of the outer body. The filter is thus collapsed down and retrieved into the reception space of the outer body. The expansible nature of the distal tip enables the tip to bend outwardly during the retrieval process to accommodate the relatively large filter together with any collected embolic material therein.

In the case of a retrieval catheter, because the inwardly tapering tip is provided as part of the outer body, misalignment between the tip and the outer body cannot occur. In addition, loading of the stent into the recess during assembly of the catheter is simplified.

In the embodiments described, misalignment of the tip and sheath is prevented. A stent is prevented from accidentally moving or deploying. The tip is conformable. The assembly operation is simplified. The distal filter has an improved abutment surface. The system has good crossing transition properties. In addition, the system can be used for retrieval of the filter.

The system may be applied to push-pull stent systems or thumb screw activated systems. It may be of the rapid exchange or over the wire type.

By providing a catheter system which has two or more functional elements, procedure time is reduced and the procedure is generally more efficiently executed. These features are achieved while providing excellent transitions, good filter abutment, trackability and safe and accurate stent deployment.

In one embodiment the inner core assembly is integral with the stent abutment surface. In another embodiment these elements can move relative to one another. In this second embodiment an alternative procedure is possible. This alternative procedure comprises placing a filter as described above and then delivering the catheter proximal to the target site. The inner core is advanced relative to the outer core and the sheath. It crosses and predilates the lesion by balloon inflation. Stent delivery and subsequent steps are as described above.

Marker bands may be placed at appropriate locations allow the clinician to accurately carry out each step of the procedure.

The system can also be applied to filter delivery by creating a filter reception space in the pod as described above. In this embodiment the distal segment of the filter provides a smooth crossing transition.

Various features of the catheter systems described may be used, as appropriate with similar systems. For example, the filter engagement feature for retrieval may be utilised in any of the catheter systems incorporating filter retrieval.

The invention is not limited to the embodiments hereinbefore described, with reference to the accompanying drawings, which may be varied in construction and detail.

The invention claimed is:

1. A catheter having an expansible internal reception space for receiving an embolic protection filter and for transporting the filter through a vasculature; and the catheter comprising a treatment device to facilitate treatment of a site in a vasculature,
wherein the catheter has an outer tubular body and an inner member extending at least partially through the outer body, the outer body having an expansible distal tip, and the inner member being movable proximally relative to the outer body from an introduction configuration to a retrieval configuration to facilitate retrieval of an embolic protection filter into the reception space;
the inner member has a proximal end and a distal end, the proximal end of the inner member has a first constant diameter, and the distal end of the inner member has a second constant diameter, the first constant diameter being larger than the second constant diameter;
a distal tip of the inner member tapers distally inwardly, the inwardly tapering distal tip of the inner member being located on the inner member at a location distal of the treatment device during the introduction configuration, the treatment device is mounted on the distal end of the inner member, and a diameter of the distal tip is greater than the second constant diameter;
the filter is separate from and slidable relative to the inner member and the outer tubular body;
a distal end of the distal tip provides a proximal stop for the filter;
the distal tip is adapted to slide completely within the outer body in the introduction configuration; and
the distal tip comprises an engagement element adapted for retrieval of the filter.

2. A catheter as claimed in claim 1 wherein the catheter comprises a delivery catheter.

3. A catheter as claimed in claim 2 wherein the inner member is movable distally relative to the outer body to deploy the filter from within the reception space.

4. A catheter as claimed in claim 3 wherein the treatment device is at least partially provided on the inner member.

5. A catheter as claimed in claim 3 wherein in the introduction configuration, the treatment device protrudes from a distal end of the outer body.

6. A catheter as claimed in claim 3 wherein the outer tubular body extends along substantially the full length of the inner member.

7. A catheter as claimed in claim 3 wherein the outer tubular body extends along part of the inner member.

8. A catheter as claimed in claim 1 wherein the catheter comprises a retrieval catheter.

9. A catheter as claimed in claim 1, wherein in the introduction configuration, the inner member protrudes from a distal end of the outer body.

10. A catheter as claimed in claim 1, wherein a distal tip of the outer body tapers distally inwardly.

11. A catheter as claimed in claim 1, wherein the distal tip of the inner member is expansible.

12. A catheter as claimed in claim 1, wherein the inner member is at least partially inflatable.

13. A catheter as claimed in claim 12 wherein the inner member comprises a balloon.

14. A catheter as claimed in claim 1 wherein the catheter defines a guidewire lumen extending at least partially therethrough for passing the catheter over a guidewire.

15. A catheter as claimed in claim 14 wherein the guidewire lumen extends only partially through the catheter to facilitate passing the catheter over a guidewire in a rapid exchange manner.

16. A catheter as claimed in claim 1 wherein the treatment device comprises an angioplasty balloon.

17. A catheter as claimed in claim 1 wherein the treatment device comprises a stent deployment balloon.

18. A catheter as claimed in claim 1 wherein the filter has a proximal and a distal end, inlet openings being positioned at the proximal end and outlet holes being positioned at the distal end.

19. A catheter as claimed in claim 18 wherein the filter is a self-expanding filter.

20. A catheter as claimed in claim 19 wherein the treatment device is a self-expanding stent.

21. A catheter as claimed in claim 19 wherein the treatment device is a balloon expandable stent.

22. A catheter as claimed in claim 1 wherein the engagement element comprises gripping formations that extend radially into a lumen of the distal tip.

23. A method for carrying out a procedure at a treatment site in a vasculature comprising the steps of
providing an embolic protection device;
deploying the embolic protection device distal of the treatment site;
providing a procedural catheter comprising a tubular member having an expansible distal space housing a medical device;
advancing the procedural catheter to the treatment site;
deploying the medical device from the procedural catheter at the treatment site;
retrieving the embolic protection device into the procedural catheter, wherein the procedural catheter has an inner member, and an expansible distal tip of the inner member tapers distally inwardly; and
the inwardly tapering distal tip of the inner member being located on the inner member at a location distal of the medical device during advancement of the procedural catheter to the treatment site,
wherein the inner member has a proximal end and a distal end, the proximal end of the inner member has a first constant diameter, and the distal end of the inner member has a second constant diameter, the first constant diameter being larger than the second constant diameter and a diameter of the distal tip is greater than the second constant diameter,
the medical device is mounted on the distal end of the inner member,
the embolic protection device is separate from and slidable relative to the inner member,
a distal end of the distal tip provides a proximal stop for the embolic protection device, and
the distal tip slides completely within the tubular member when the embolic protection device is retrieved, and
the embolic protection device is retrieved into the procedural catheter by engaging the embolic protection device with gripping formations on the distal tip and then pulling proximally on the inner member.

24. A method as claimed in claim 23 wherein the medical device is a stent; the procedural catheter is a stent delivery catheter having a distal reception space housing a stent; and the method comprises deploying the stent from the stent delivery catheter; and retrieving the embolic protection device at least partially into the reception space in the stent delivery catheter.

25. A method as claimed in claim 24 wherein the stent is a self expanding stent.

26. A method as claimed in claim 24 wherein the stent is a balloon expandable stent.

27. A method as claimed in claim 23 wherein the procedural catheter comprises a balloon catheter and the method comprises deploying the balloon at the treatment site.

28. A method as claimed in claim 27 wherein the balloon is a post dilatation balloon.

29. A method as claimed in claim 27 wherein the balloon is a stent expanding balloon.

30. A method as claimed in claim 23, wherein the inner member is a centering member which projects distally of a distal end of the procedural catheter.

31. A method as claimed in claim 23, wherein the inner member comprises an engagement element for engagement with an embolic protection device.

32. A method as claimed in claim 23 comprising advancing a guidewire through the vasculature so that a distal tip of the guidewire is located distal of the treatment location, and then advancing the catheter over the guidewire.

33. A method as claimed in claim 23 wherein after engaging the embolic protection device with the gripping formations, the inner member is moved proximally, relative to the tubular member, to capture the embolic protection device.

* * * * *